United States Patent [19]

Imai et al.

[11] 4,217,305
[45] Aug. 12, 1980

[54] PHENYLETHANOLAMINE DERIVATIVES

[75] Inventors: Kazuo Imai, Omiya; Kunihiro Niigata, Ageo; Takashi Fujikura, Hachioji; Shinichi Hashimoto, Matsudo; Toichi Takenaka, Tokyo, all of Japan

[73] Assignee: Yamanouchi Pharmaceutical Co., Ltd., Tokyo, Japan

[21] Appl. No.: 946,192

[22] Filed: Sep. 27, 1978

[30] Foreign Application Priority Data

Oct. 12, 1977 [JP]   Japan .................................. 52-122034
Oct. 26, 1977 [JP]   Japan .................................. 52-128436
Dec. 23, 1977 [JP]   Japan .................................. 52-155352
Jun. 21, 1978 [JP]   Japan .................................. 53-74964

[51] Int. Cl.² .................... C07C 143/78; A61K 31/18; A61K 31/335; C07D 319/18
[52] U.S. Cl. .......................... 260/556 AR; 260/340.3; 260/340.5 R; 260/397.7 R; 260/397.7 DS; 260/465 D; 260/465 E; 260/501.17; 260/501.19; 260/556 B; 260/556 C; 260/556 S; 424/228; 424/229; 424/278; 424/282; 424/304; 424/316; 424/321
[58] Field of Search ........ 260/556 AR, 556 B, 556 C, 260/556 S, 340.5 R, 340.3, 397.7 R, 501.17, 501.19, 397.7 DS, 465 E, 465 D

[56] References Cited

U.S. PATENT DOCUMENTS

| | | | |
|---|---|---|---|
| 3,701,808 | 10/1972 | Hartley et al. ........... | 260/556 AR X |
| 3,711,545 | 1/1973 | Kaiser et al. .................... | 260/556 N |
| 3,860,647 | 1/1975 | Colella et al. ................ | 260/556 AR |
| 4,034,112 | 7/1977 | Smith ........................ | 260/556 AR X |
| 4,038,314 | 7/1977 | Mentrup et al. ................. | 260/556 N |
| 4,140,713 | 2/1979 | Oxford et al. ................ | 260/556 AR |

FOREIGN PATENT DOCUMENTS 1266058 of 0000 United Kingdom .
1321701 of 0000 United Kingdom .

Primary Examiner—Thomas A. Waltz
Attorney, Agent, or Firm—Burgess, Ryan and Wayne

[57]          ABSTRACT

Novel phenylethanolamine derivatives represented by the formula

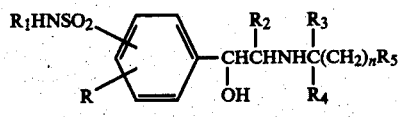

wherein R represents a hydrogen atom, a halogen atom, a hydroxyl group, a lower alkyl group, a lower alkoxy group, a lower alkylthio group, an amino group, a lower acylamino group, a lower alkylsulfonyl group, or a lower alkylsulfonylamino group; $R_1$, $R_2$, $R_3$ and $R_4$, which may be the same or different, each represents hydrogen or a lower alkyl group; $R_5$ represents an aryl group which may have a substituent, a benzodioxane ring group which may have a substituent, an aryloxy group which may have a substituent, or an arylthio group which may have a substituent; said $R_5$ being, however, a benzodioxane ring group which may have a substituent, an aryloxy group which may have a substituent, or an arylthio group which may have a substituent when R is a hydroxyl group; and n represents 0 or an integer of 1–3 and the acid addition salts thereof.

The compounds of this invention exhibit α- and β-adrenergic blocking actions and are useful as antihypertensive agents.

9 Claims, No Drawings

PHENYLETHANOLAMINE DERIVATIVES

BACKGROUND OF THE INVENTION

1. Field of the Invention

The invention relates to novel phenylethanolamine derivatives and the acid addition salts thereof and more particularly, it relates to novel phenylethanolamine derivatives and the acid addition salts thereof which exhibit α- and β-adrenergic blocking actions and are useful as antihypertensive agents with less side effects. The invention further relates to a process of producing these compounds.

2. Description of the Prior Art

British Pat. No. 1,321,701 discloses a series of compounds represented by the following formula

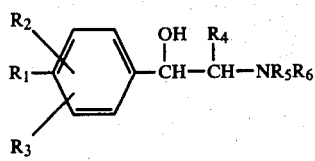

wherein $R_1$ is RS, RSO or $RSO_2$ (wherein R is an alkyl group of 1–10 carbon atoms); $R_2$ and $R_3$ each is a hydrogen atom, an alkoxy group of 1–4 carbon atoms, or an alkylthio group of 1–4 carbon atoms; $R_4$ is a hydrogen atom or an alkyl group of 1–4 carbon atoms; and $R_5$ and $R_6$ each is an alkyl group of 1–16 carbon atoms substituted by a phenyl group or a substituted phenyl group, and it is described in the patent specification that these compounds exhibit β-adrenergic blocking action, peripheral vasodilating effect, antiarrhythmic effect and hypotensive effect.

U.S. Pat. No. 3,860,647 discloses a series of compounds represented by the following formula

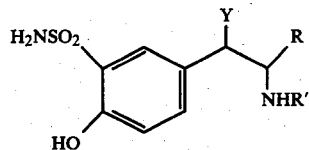

wherein R is hydrogen atom or an alkyl group of 1–4 carbon atoms; R' is an alkyl group of 1–6 carbon atoms, a cycloalkyl group of 3–6 carbon atoms, $XC_6H_4(CH_2)_2CH(CH_3)$, $XC_6H_4(CH_2)_2C(CH_3)_2$, $XC_6H_4CH_2CH(CH_3)$, or $XC_6H_4CH_2C(CH_3)_2$ (wherein X is hydrogen atom, a hydroxy group, or a methoxy group); and Y is a hydrogen atom or a hydroxyl group, and it is described therein that these compound exhibit β-adrenergic blocking action.

Also, British Pat. No. 1,266,058 discloses a series of compounds represented by the following formula

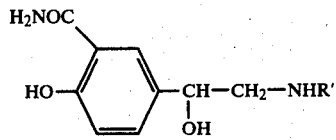

wherein R' is an aralkyl or aryloxyalkyl group optionally substituted by one or more OH or O-alkyl groups in the aryl residue, and it is described therein that these compounds exhibit α- and β-adrenergic blocking actions and are useful as drugs for treatment of hypertension and angina pectoris.

In the field of treatment of hypertension, the employment of peripheral vasodilators for hypotensive purposes encounters a serious disadvantage in that there occurs a reflex tachcardia induced by the decrease of the blood pressure. Recently, an effort for overcoming this difficulty has been made by using peripheral vasodilators together with β-adrenergic blocking agents possessing an action for controlling reflex tachcardia but this treatment system is objectionable in that two different kinds of medicaments are required and they must be administrated separately.

SUMMARY OF THE INVENTION

An object of this invention is, therefore, to provide a pharmaceutically useful compound which has a hypotensive effect due to peripheral vasodilation (α-adrenergic blocking action) and β-adrenergic blocking action and can be used as an antihypertensive agent without accompanied by the undesirable secondary effect of causing reflex tachcardia as in the case of employing conventional vasodilators.

Another object of this invention is to provide a process of producing the aforesaid pharmaceutically useful compound.

That is, according to this invention, there is provided phenylethanolamine derivatives represented by the formula

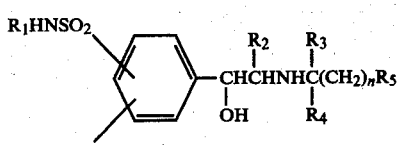

wherein R represents a hydrogen atom, a halogen atom, a hydroxyl group, a lower alkyl group, a lower alkoxy group, a lower alkylthio group, an amino group, a lower acylamino group, a lower alkylsulfonyl group, or a lower alkylsulfonylamino group; $R_1$, $R_2$, $R_3$ and $R_4$, which may be the same or different, each represents hydrogen atom or a lower alkyl group; $R_5$ represents an aryl group which may have a substituent, a benzodioxane ring group which may have a substituent, an aryloxy group which may have a substituent, or an arylthio group which may have a substituent; said $R_5$ being, however, a benzodioxane ring group which may have a substituent, an aryloxy group which may have a substituent, or an arylthio group which may have a substituent when R is a hydroxyl group; and n represents 0 or an integer of 1–3 and the acid addition salts thereof.

The compounds of this invention are useful as antihypertensive agents.

According to another embodiment of this invention, there is further provided a process of producing the phenylethanolamine derivatives represented by the aforesaid formula I by reacting the halohydrin represented by the formula

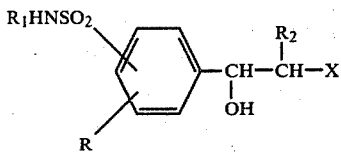

and the amine represented by the formula

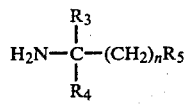

wherein R, $R_1$, $R_2$, $R_3$, $R_4$, $R_5$, and n have the same significance as in formula I and X represents a halogen atom, or by reacting the epoxide represented by the formula

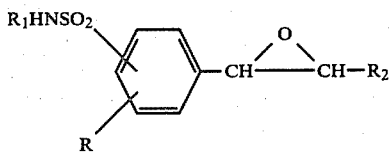

and the amine represented by the formula

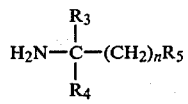

wherein R, $R_1$, $R_2$, $R_3$, $R_4$, $R_5$, and n have the same significance as in formula I, or by reducing the aminoketone represented by the formula

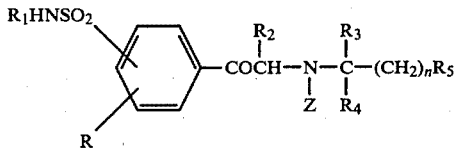

wherein R, $R_1$, $R_2$, $R_3$, $R_4$, $R_5$, and n have the same siginificance and Z represents a hydrogen atom or a benzyl group and, when Z is a benzyl group, removing the group from the product.

DESCRIPTION OF THE PREFERRED EMBODIMENTS

Now, the term "lower" used in the above-described formulae means a straight or branched carbon chain having 1 to 5 carbon atoms. Therefore, for example, a lower alkyl group includes a methyl group, ethyl group, propyl group, butyl group, pentyl group, isobutyl group, etc., and a lower alkoxy group includes a methoxy group, ethoxy group, propoxy group, butoxy group, etc. Also, examples of the aryl group, aryloxy group, and arylthio group represented by $R_5$ of the above-described formulae are, for example, a phenyl group, a naphthyl group, a phenyloxy group, a phenylthio group, etc. These groups represented by $R_5$ or the benzodioxane ring group which is another group shown by $R_5$ may have a substituent and examples of such a substituent are, for example, a hydroxyl group, a lower alkoxy group, a lower alkyl group, halogen atom, a cyano group, a carbamoyl group, an aryl group, an aryloxy group, a methylenedioxy group ($-O-CH_2-O-$), an ethylenedioxy group ($-O-CH_2-CH_2-O-$), a lower acyl group, etc. Also, in the above-described formulae, the sulfamoyl group ($-SO_2NHR_1$) and R which are substituents of the benzene ring may be disposed at positions ortho, meta, and para to the side chain. Furthermore, since the compounds of formula I of this invention can form readily salts and contain at least one asymmetric carbon atom, the compounds of this invention include the salt thereof, the racemic compound thereof, a mixture of the racemic compounds, and each optical active substance.

In the specification of this invention, when the carbon atoms are denoted by $*_1$ and $*_2$ relative to the isomers in the following compounds of formulae (A), (B), and (C) are an asymmetric carbon atom, the racemic compound and the racemic mixture are referred to as $i_1$ and $i_2$ and when the carbon atoms are denoted by $*_3$ and $*_4$, the racemic compound and the racemic mixture are referred to as $i_1'$ and $i_2'$;

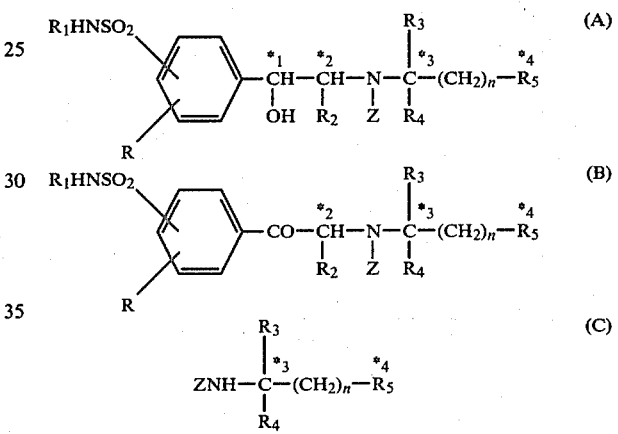

wherein Z represents a hydrogen atom or a benzyl group and R, $R_1$, $R_2$, $R_3$, $R_4$, $R_5$ and n have the same siginificance as in formula I.

The compounds of formula I and the acid addition salts thereof provided by the present invention exhibit both α- and β-adrenergic blocking agents. Therefore, they can be utilized for various treatments. For example, they can be used as antihypertensive agents with less untoward side effects, for the treatment of peripheral vascular disorders such as Raynaud's disease and for the treatment of angina pectoris, arrhythmia and migraine headaches.

The pharmacological effects of the compounds of this invention were determined by the following experiments. The effects of the typical compounds of this invention were compared with those of 5-[1-hydroxy-2-(1-methyl-3-phenyl-propyl)aminoethyl]salicylamide (general name; labetalol) which is one of the typical compounds discloses in British Pat. No. 1,266,058.

A. α-Adrenergic blocking action:

(a) The blood pressure was measured in rats anesthetized with urethane and treated with pentolinium. The effects of the test samples (intravenous injection) to antagonize the hypertensive response to phenylephrine (10 μg/Kg i.v.) were measured and the results were shown in Table I.

(b) β-Adrenergic blocking action:

The β-adrenergic blocking property was measured according to the Tachikawa, Takenaka, et al, method [Yakugaku-Zasshi, 93(12), 1573–1580 (1973)]. Heart rate was measured in rats which were pretreated with reserpine (8 mg/Kg i.p.) 18 hrs. before the experiment and anesthetized with pentobarbital (55 mg/Kg i.p.). Bilateral vagotomy was performed at the neck. The effects of the test samples to antagonize the isoproterenol (0.1 μg/Kg iv.) induced tachycardia were measured and the results were shown in Table I.

B. Antihypertensive effects in spontaneously hypertensive rats:

Intravenous administration: The systolic blood pressure and heart rate were measured by direct recording of blood pressure in conscious spontaneously hepertensive rats having a systolic blood pressure of higher than 150 mmHg according to the Mizoguchi et al method [Nippon Taishitsugaku-Zasshi, 32, 59–63 (1969)].

Oral administration: The systolic blood pressure was measured indirectly from the tail using a programmed electro-sphygmanometer (Nacro Bio-Systems Inc., PE-300) on spontaneously hypertensive rats having a systolic blood pressure of higher than 150 mmHg, the result being shown in Table II.

| Sample | α-, β-blocking activity | |
|---|---|---|
| | α-blocking (Rat) $ED_{50}$ (mg/Kg)i.v. | β-blocking (Rat) $ED_{50}$ (mg/Kg)i.v. |
| Compounds of this invention (Example No.) | | |
| 9 | 0.89 | 0.26 |
| 13 | 0.23 | 0.014 |
| 15 | 0.13 | 0.15 |
| 25 | 1.3 | 0.035 |
| 28 | 1.1 | 0.42 |
| 30 | 1.8 | 0.052 |
| 34 | 0.068 | 0.28 |
| 36($i_1 + i_2$) | 0.43 | 0.095 |
| 36($i_1$) | 1.2 | 0.071 |
| 36($i_2$) | 0.093 | 0.41 |
| 39 | 0.066 | 0.27 |
| 41 | 0.66 | 0.044 |
| 43 | 0.0091 | 0.53 |
| 45 | 0.86 | 0.013 |
| 47 | 0.034 | 0.16 |
| 50 | 0.30 | 0.049 |
| 52 | 1.1 | 0.022 |
| 63 | 0.27 | 0.080 |
| 64 | 0.20 | 0.12 |
| 69($i_1 + i_2$) | 0.27 | 0.083 |
| 69($i_1$) | 0.24 | 0.057 |
| 69($i_2$) | 0.054 | 0.47 |
| Known compound | | |
| Labetalol | 1.1 | 0.11 |

| | antihypertensive effect |
|---|---|
| Sample | change in systolic blood pressure (mmHg) at 10 mg/Kg p.o. |
| Compounds of this invention (Example No.) | |
| 9 | $-25 \pm 4.2$ |
| 15 | $-11 \pm 4.3$ |
| 18 | $-34 \pm 5.2$ |
| 24 | $-27 \pm 6.1$ |
| 28($i_1$) | $-23 \pm 4.3$ |
| 34 | $-20 \pm 4.3$ |
| 36($i_1 + i_2$) | $-40 \pm 6.6$ |
| 36($i_1$) | $-18 \pm 6.1$ |
| 36($i_2$) | $-33 \pm 5.7$ |
| 39 | $-11 \pm 5.5$ |
| 41 | $-30 \pm 4.9$ |
| 43 | $-33 \pm 6.9$ |
| 46 | $-20 \pm 4.5$ |
| 47 | $-35 \pm 6.4$ |
| 48 | $-49 \pm 4.9$ |
| 60 | $-31 \pm 2.8$ |
| 61 | $-54 \pm 5.4$ |
| 62 | $-47 \pm 6.6$ |
| 69($i_1 + i_2$) | $-43 \pm 5.8$ |
| 69($i_1$) | $-28 \pm 7.7$ |
| 69($i_2$) | $-32 \pm 6.7$ |
| 70($i_1'$) | $-27 \pm 6.1$ |
| 71 | $-27 \pm 6.2$ |
| 72($i_1'$) | $-30 \pm 4.3$ |
| Known compound | |
| Labetalol | $-10 \pm 3.6$ |

Values are mean ± S.E. of 5 to 10 animals.

The clinical administration of the compounds of this invention is usually practiced by intravenous injection or orally as the free bases or the acid addition salts thereof (e.g., hydrochlorides, sulfates, maleates, acetates, fumarates, lactates, citrates, etc.,). It is proper to administer a 10–50 mgs dose of the compound several times a day in case of intravenous administration or 50–300 mg of the compound three times a day in case of oral administration.

The compounds of this invention may be formulated into ordinary dosage forms such as, for example, tablets, capsules, pills, solutions, etc., and in these cases, the medicaments can be prepared by conventional methods using usual medical excipients.

The compounds of this invention shown by formula I can be produced by the following processes.

Process 1

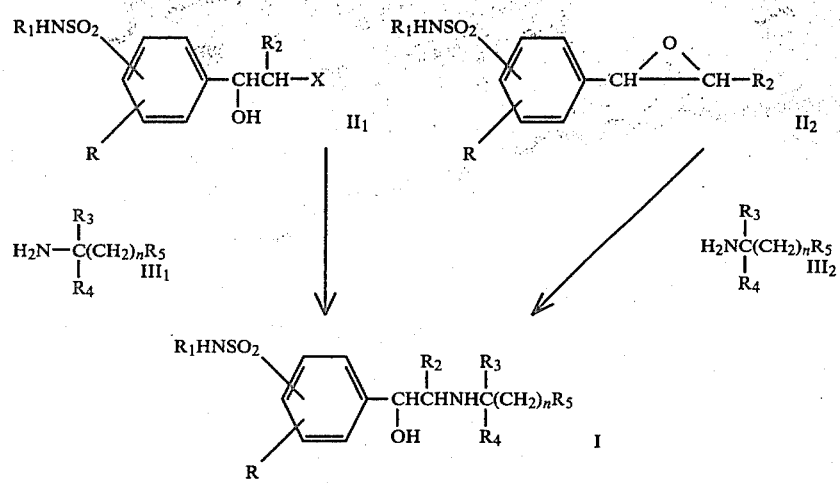

wherein X represents a halogen atom and R, $R_1$, $R_2$, $R_3$, $R_4$, $R_5$ and n have the same significance as above.

In the process, the desired compounds of formula I are produced by aminating the halohydrin of formula $II_1$ or the epoxide of formula $II_2$ with the amine of formula $III_1$. These reactions can be carried out under almost the same conditions.

The reaction is usually performed by reacting the halohydrin of formula $II_1$ or the epoxide of formula $II_2$ with an equimolar amount or excessive amount of the amine of formula $III_1$ in an organic solvent. As the organic solvent used in the reaction, there are illustrated ethanol, toluene, methyl ethyl ketone, acetonitrile, tetrahydrofuran, etc. Also, the reaction proceeds at room temperature or under heating but the reaction is usually carried out under refluxing to accelerate the reaction.

The reaction product formed can be isolated and purified using an extraction by solvent, separation by column chromatography, crystallization, etc.

Process 2

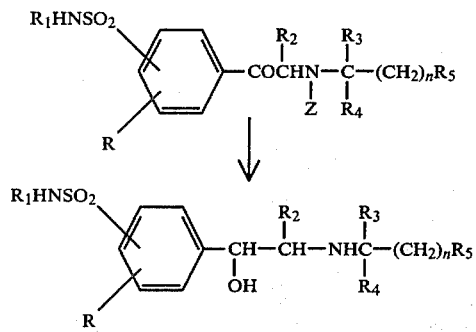

wherein Z represents a hydrogen atom or a benzyl group as a protective group and R, $R_1$, $R_2$, $R_3$, $R_4$, $R_5$ and n have the same significance as above.

In the process, the desired compound of formula I is produced by reducing the aminoketone of formula $II_3$. That is:

(i). The desired compound of formula I is obtained by reducing the ketone group (—CO—) at the side chain of the aminoketone of formula $II_3$ into the —CHOH group using a suitable reducing agent such as a complex metallic hydride compound, for example, sodium borohydride, diborane. The reduction is performed in an organic solvent under cooling or at room temperature.

When Z is a benzyl group as the protective group, the benzyl group is not influenced in the case of reducing the aminoketone using the aforesaid reducing agent and hence in order to remove the benzyl group, the catalytic hydrogenation is performed by a conventional manner using palladium charcoal as the catalyst after the reduction.

(ii). In another process, the reduction is performed by subjecting the aminoketone of formula $II_3$ to a catalytic hydrogenation in the presence of a conventional hydrogenation catalyst such as palladium charcoal, whereby the reduction of the carbonyl group at the side chain and the debenzylation are performed at the same time even when Z is a benzyl group as the protective group.

The desired compound of formula I thus formed possesses at least one asymmetric carbon atom or, in the maximum case, four asymmetric carbon atoms (i.e., the case when the carbon atoms denoted by $*_1$, $*_2$, $*_3$ and $*_4$ L described above are all asymmetric carbon atoms) and hence there are isomers thereof. In the isomers of formula I, the separation of the racemic compounds or racemic mixtures($i_1$, $i_2$) when the carbon atoms of $*_1$ and $*_3$ are asymmetric carbon atoms and the separation of racemic mixtures($i_1'$, $i_2'$) when the carbon atoms of $*_3$ and $*_4$ are asymmetric carbon atoms are performed in a conventional manner such as fractional crystallization or can be easily practiced, by other methods, as by separating the benzyl derivative of formula I using a silica gel column chromatography and then subjecting the benzyl derivative to debenzylation. Also, the separation of the racemic mixture of the desired compound of this invention may be attained by selecting beforehand one of the isomers $i_1'$ and $i_2'$ for the raw material of formula $III_1$.

Now, the production process of the compounds of this invention shown by formula I were explained above and typical examples of the compounds obtained by the process are as follows:

5-{1-Hydroxy-2-[2-(2-methoxyphenoxy)-1-methylethylamino]-ethyl}-2-methylbenzenesulfonamide.

5-{1-Hydroxy-2-[2-(2-methoxyphenoxy)-1-methylethylamino]-ethyl}-2-methoxybenzenesulfonamide.

2-Hydroxy-5-{1-hydroxy-2-[2-(2-methoxyphenoxy)-1-methylethylamino]ethyl}benzenesulfonamide.

5-{1-Hydroxy-2-[2-(2-methoxyphenoxy)ethylamino]ethyl}-2-methylbenzenesulfonamide.

5-{1-Hydroxy-2-[3-(2-methoxyphenyl)-1-methylpropylamino]-ethyl}-2-methylbenzenesulfonamide.

2-Hydroxy-5-{1-hydroxy-2-[2-(2-methoxyphenoxy)ethylamino]-ethyl}benzenesulfonamide.

5-{1-Hydroxy-2-[2-(2-hydroxyphenoxy)-1-methylethylamino]-ethyl}-2-methylbenzenesulfonamide.

5-{1-Hydroxy-2-[2-(2-ethoxyphenoxy)-1-methylethylamino]-ethyl}-2-methylbenzenesulfonamide.

5-{1-Hydroxy-2-[2-(2-ethoxyphenoxy)ethylamino]ethyl}-2-methylbenzenesulfonamide.

5-{1-Hydroxy-2-[2-(2-ethoxyphenoxy)ethylamino]ethyl}-2-methoxybenzenesulfonamide.

5-{1-Hydroxy-2-[2-(2-hydroxymethylphenoxy)ethylamino]ethyl}-2-methylbenzenesulfonamide.

2-Hydroxy-5-{1-hydroxy-2-[2-(2-ethoxyphenoxy)ethylamino]ethyl}benzenesulfonamide.

5-{1-Hydroxy-2-[2-(2-methoxyphenoxy)ethylamino]ethyl}-2-methoxybenzenesulfonamide.

5-{1-Hydroxy-2-[2-(2-ethoxy-4-hydroxymethylphenoxy)ethylamino]ethyl}-2-methylbenzenesulfonamide.

5-{1-Hydroxy-2-[2-(2-hydroxyphenoxy)ethylamino]ethyl}-2-methylbenzenesulfonamide.

Then, the production process of this invention will be further described in the following examples more practically. In addition, the starting materials of formula III₁ used in the process of this invention include novel compounds and examples of the production of these compounds are shown in the following reference examples.

Reference example 1:

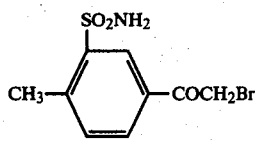

(1). To 400 ml of a mixture of acetic acid and concentrated hydrochloric acid in a 1:1 by volume ratio was added 54 g of 3-amino-4-methylacetophenone. After cooling the mixture to 0° C., a solution of 42 g of sodium nitrite in 100 ml of water was added dropwise to the mixture at 0°-2° C. Thereafter, the mixture was stirred for 20 minutes at 0° C., cooled to −10° C. to −5° C., and then a cold solution of 20 g of cupric chloride dihydrate and 120 g of sulfur dioxide dissolved in 300 ml of acetic acid was added quickly to the mixture.

Then, after stirring the resultant mixture for 3 hours at room temperature, 250 ml of water was added to the mixture and the reaction product was extracted with 800 ml of benzene. The benzene layer recovered was washed with water, dried over anhydrous magnesium sulfate, and after removing the anhydrous magnesium sulfate, the solvent was distilled off under reduced pressure to provide a brown oily matter. To the oily matter was added 250 ml of aqueous ammonia under cooling. The mixture was stirred overnight at room temperature to precipitate crystals. The crystals were recovered by filtration, washed with water and dried to provide 61 g of crude 5-acetyl-2-methylbenzenesulfonamide. The crude product was recrystallized from isopropanol. The melting point of the product thus obtained was 144°-146° C.

(2). To 480 ml of acetic acid was added 50 g of 5-acetyl-2-methylbenzenesulfonamide. The mixture was heated with stirring until the sulfonamide was completely dissolved. Then, the heating was stopped, 38 g of bromine was added dropwise to the mixture followed by stirring for 20 minutes and then acetic acid was distilled off under reduced pressure. Thus, crystals were precipitated and after distilling off acetic acid almost completely, 50 ml of ether was added. After washing well the crystals, they were recovered by filtration. The crystals were further washed with ether and dried to provide 52 g of colorless crystals of 5-bromoacetyl-2-methylbenzenesulfonamide having a melting point of 144.5°-146.5° C.

Reference example 2:

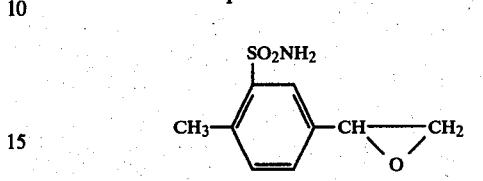

In 200 ml of methanol was dissolved 10 g of 5-bromoacetyl-2-methylbenzenesulfonamide. Then, 6.5 g of sodium borohydride was added gradually to the solution. After stirring the mixture for 2.5 hours at room temperature, methanol was distilled off under reduced pressure, 100 ml of water was added to the residue, and the reaction product was extracted three times each time with 100 ml of ethyl acetate. The ethyl acetate layer was separated, dried with anhydrous magnesium sulfate and ethyl acetate was distilled off under reduced pressure to provide 6.2 g of the pale yellow crystals of 5-epoxyethyl-2-methylbenzenesulfonamide having a melting point of 151°-153° C.

Reference example 3:

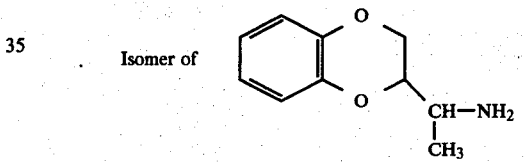

Isomer of (1). In 100 ml of isopropanol were dissolved 35.4 g (0.02 mole) of 2-acetyl-1,4-benzodioxane and 25.6 g (0.024 mole) of benzylamine. And after adding 0.02 g of platinum oxide to the solution, hydrogenation was performed by a catalytic reduction at normal pressure until absorption stopped. The platinum oxide was filtered off and the filtrate was distilled under reduced pressure to provide 37.0 g. of crude N-benzyl-1-(1,4-benzodioxan-2-yl)ethylamine having a boiling point of 150°-165° C./0.7 mmHg.

(2). In 200 ml of ether was dissolved 13.5 g of crude N-benzyl-1-(1,4-benzodioxan-2-yl)ethylamine. Then, 100 ml of 1 normal hydrochloric acid was added to the solution followed by shaking. Then, the ether layer was immediately removed and 100 ml of ether was added to the solution followed by stirring at room temperature to form colorless crystals. The mixture was allowed to stand for 3 days in an ice-chamber and crystals were recovered by filtration to provide crude N-benzyl-1-(1,4-benzodioxan-2-yl)ethylamine hydrochloride (isomer i₁'). By recrystallizing the crude product from 20 ml of water, 4.5 g of pure N-benzyl-1-(1,4-benzodioxan-2-yl)ethylamine hydrochloride having a melting point of 178°-180° C. was obtained. The product was converted into a base by a conventional manner followed by distillation to provide 3 g of pure N-benzyl-1-(1,4-benzodioxan-2-yl)ethylamine (isomer i₁') base.

On the other hand, the aqueous layer was recovered from the above filtrate and after converting the product therein into the base by a conventional manner, the solution was subjected to a silica gel column chromatography having packed therein 200 ml of silica gel using a mixture of chloroform and ethyl acetate of 3:1 by volume ratio as the eluting solvent. The residual base $i_1'$ was completely eluted and then crude N-benzyl-1-(1,4-benzodioxan-2-yl)ethylamine (isomer $i_2'$) base was eluted. The fractions containing the isomer $i_2'$ were collected and after distilling off the solvent, the residue was distilled under reduced pressure to provide 2.5 g of pure N-benzyl-1-(1,4-benzodioxan-2-yl)ethylamine (isomer $i_2'$) base having a boiling point of 165°–168° C./0.8 mmHg.

(3). In 50 ml of methanol was dissolved 7 g of pure N-benzyl-1-(1,4-benzodioxan-2-yl)ethylamine ($i_1'$). After adding one drop of ethanolic hydrochloric acid and 0.5 g of 10% palladium charcoal to the solution, and catalytic reduction was performed at normal pressure until the absorption of hydrogen gas stopped. Then, palladium charcoal was filtered away, the filtrate was acidified with the addition of ethanolic hydrochloric acid, and the solvent was distilled off. Then, 20 ml of isopropanol was added to the residue and the product formed was recovered by filtration to provide 4.4 g (75.7%) of 1-(1,4-benzodioxan-2-yl)ethylamine ($i_1'$) hydrochloride having a melting point of 234°–235° C. The product was then converted into a base by a conventional manner and distilled under reduced pressure to provide 2.9 g (62.3%) of 1-(1,4-benzodioxan-2-yl)ethylamine ($i_1'$) having a boiling point of 88°–90° C./0.1 mmHg.

Reference example 4:

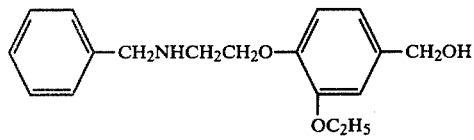

(1). While stirring a mixture of 30 g of 3-ethoxy-4-hydroxybenzyl alcohol, 125 g of anhydrous potassium carbonate, and 600 ml of methyl ethyl ketone, 168 g of 1,2-dibromoethane was added to the mixture, and the resultant mixture was refluxed for 48 hours with stirring. After cooling, the reaction mixture was filtered under suction and the filtrate was distilled under reduced pressure to provide a pale-yellow oily matter. The product was dissolved in 300 ml of ether and the solution was washed twice each with 50 ml of an aqueous 5% sodium hydroxide solution and then with 50 ml of water, dried with anhydrous sodium sulfate, and distilled under reduced pressure to provide a yellow oily matter. To the product was added 100 ml of a mixture of ether and petroleum ether of 1:1 by volume ratio to form crystals, which were recovered by filtration under suction to provide 39 g of 3-ethoxy-4-(2-bromoethoxy)benzyl alcohol having a melting point of 51°–53° C.

(2). A mixture of 27.5 g of 3-ethoxy-4-(2-bromoethoxy)benzyl alcohol and 53.5 g of benzylamine was heated to 130°–135° C. for 1.5 hours with stirring. After cooling the reaction mixture, 300 ml of ethyl acetate was added therein and the mixture was washed twice each time with 50 ml of water, dried with anhydrous sodium sulfate and distilled under reduced pressure to provide an orange oily product. To the product was added 50 ml of acetone to form crystals, which were recovered by filtration under suction to provide 22.5 g of N-benzyl-2-(2-ethoxy-4-hydroxymethylphenoxy)ethylamine having a melting point of 164°–167° C.

Reference example 5:

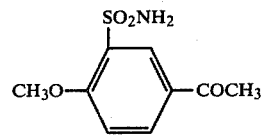

After cooling 200 g of chlorosulfonic acid to 0°–5° C., 30 g of 4-methoxyacetophenone was added gradually to the acid with stirring. The mixture was stirred overnight at room temperature and then heated to 50°–60° C. for 3 hours. After cooling, the reaction mixture was poured into ice pieces and the crystals thus precipitated were extracted with 500 ml of ethyl acetate. The ethyl acetate layer recovered was washed with water, dried with anhydrous magnesium sulfate, and after removing the anhydrous magnesium sulfate, the solvent was distilled off under reduced pressure to provide 37.1 g of a pale-yellow solid product. The product was dissolved in 150 ml of tetrahydrofuran and after adding thereto 300 ml of aqueous ammonia under cooling, the mixture was stirred overnight to form crystals, which were recovered by filtration, washed with water, and dried to provide 25 g of 5-acetyl-2-methoxybenzenesulfonamide having a melting point of 207°–209° C.

EXAMPLE 1

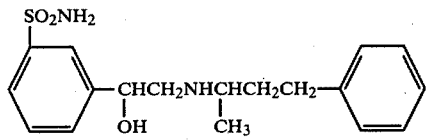

A mixture of 3.3 g of 1-methyl-3-phenylpropylamine, 50 ml of ethanol, and 2.5 g of 3-(2-bromo-1-hydroxyethyl)benzenesulfonamide was refluxed for 4 hours with stirring. After cooling the reaction mixture, ethanol was distilled off under reduced pressure. The residue was dissolved in 50 ml of benzene and after filtering off the crystals precipitated, benzene was distilled off under reduced pressure. Then, the viscous oily matter thus obtained was subjected to a silica gel column chromatography and eluted by a mixture of chloroform and methanol of 8.5:1.5 by volume ratio to provide 1.1 g of a viscous oily matter.

The oily matter was subjected again to a silica gel column chromatography and eluted with a mixture of ethyl acetate and methanol of 9:1 by volume ratio to provide 0.4 g of the amorphous powder of 3-[1-hydroxy-2-(1-methyl-3-phenylpropylamino)ethyl]benzenesulfonamide. The product had the following physical and chemical properties.

(1) Amorphous form
(2) Elemental analysis for $C_{18}H_{24}N_2O_3S$:

|  | C(%) | H(%) | N(%) |
| --- | --- | --- | --- |
| Calculated: | 62.04 | 6.94 | 8.04 |
| Found: | 62.13 | 6.88 | 8.06 |

(3) Nuclear magnetic resonace spectra (CDCl$_3$) ppm:
1.03 (3H, d, CHC$\underline{H}_3$); 4.66 (1H, m, C$\underline{H}$OH).

EXAMPLE 2

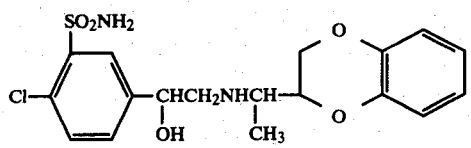

In 20 ml of ethanol were dissolved the isomer (i$_1'$) of 2.1 g (0.012 mole) of 1-(1,4-benzodioxan-2-yl)ethylamine and 1.4 g (0.006 mole) of 2-chloro-5-epoxyethylbenzenesulfonamide. The solution was refluxed for 3 hours with stirring and ethanol was distilled off under reduced pressure to provide a viscous oily product. The product was subjected to a silica gel column chromatography and purified using ethyl acetate as the eluting solvent. Then, ethyl acetate was completely distilled off under reduced pressure to provide 1.1 g of the caramel-like isomer (i$_1'$) of 2-chloro-5-{1-hydroxy-2-[1,4-benzodioxan-2-yl)ethylamino]ethyl}benzenesulfonamide. The product had the following physical and chemical properties.
(1) Amorphous form
(2) Elemental analysis for C$_{18}$H$_{21}$N$_2$O$_5$SCl:

|  | C(%) | H(%) | N(%) |
|---|---|---|---|
| Calculated: | 52.36 | 5.13 | 6.78 |
| Found: | 52.09 | 5.21 | 6.52 |

(3) Nuclear magnetic resonance spectra (CDCl$_3$) ppm:
1.12 (3H, d, CHC$\underline{H}_3$); 4.67 (1H, q, C$\underline{H}$OH).
(4) Mass spectrum: 412 (M+).

By the similar procedure as in Example 2, the compounds of the following Examples 3-9 were produced.

In the physical and chemical properties in Examples, mp represents a melting point, Anal. represents the elemental analysis, NMR represents nuclear magnetic resonance spectra, and Mass represents a mass spectrum.

EXAMPLE 3

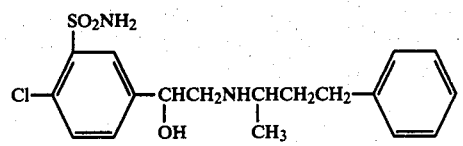

2-Chloro-5-[1-hydroxy-2-(1-methyl-3-phenyl-propylamino)-ethyl]benzenesulfonamide
Physical and chemical properties
(1) Amorphous form
(2) Anal. (C$_{18}$H$_{23}$N$_2$O$_3$SCl)

|  | C(%) | H(%) | N(%) |
|---|---|---|---|
| Calcd.: | 56.46 | 6.05 | 7.32 |
| Found: | 56.67 | 6.18 | 7.29 |

(3) NMR (CDCl$_3$) ppm:
1.05 (3H, d, CHC$\underline{H}_3$), 4.60 (1H, q, C$\underline{H}$OH)
(4) Mass 382 (M+)

EXAMPLE 4

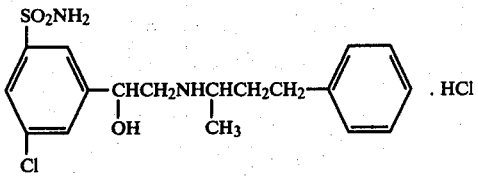

3-Chloro-5-[1-hydroxy-2-(1-methyl-3-phenyl-propylamino)-ethyl]benzenesulfonamide hydrochloride
Physical and chemical properties
(1) Amorphous form
(2) Anal. (C$_{18}$H$_{23}$N$_2$O$_3$SCl.HCl)

|  | C(%) | H(%) | N(%) |
|---|---|---|---|
| Calcd.: | 51.55 | 5.77 | 6.68 |
| Found: | 51.35 | 5.74 | 6.41 |

(3) NMR (CDCl$_3$+D$_2$O+Na$_2$CO$_3$) ppm:
1.09 (3H, d, CHC$\underline{H}_3$), 4.72 (1H, m, C$\underline{H}$OH).

EXAMPLE 5

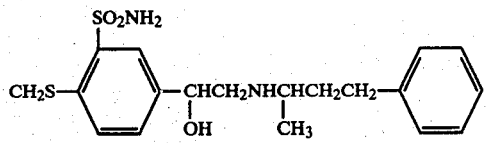

5-[1-Hydroxy-2-(1-methyl-3-phenylpropylamino)ethyl]-2-methylthiobenzenesulfonamide
Physical and chemical properties
(1) mp 109°-110° C.
(2) Anal. (C$_{19}$H$_{26}$N$_2$O$_3$S$_2$)

|  | C(%) | H(%) | N(%) |
|---|---|---|---|
| Calcd.: | 57.84 | 6.64 | 7.10 |
| Found: | 57.54 | 6.77 | 6.93 |

(3) NMR (CDCl$_3$) ppm:
1.12 (3H, d, CHC$\underline{H}_3$), 2.53 (3H, s, SCH$_3$), 4.70 (1H, m, C$\underline{H}$OH).

EXAMPLE 6

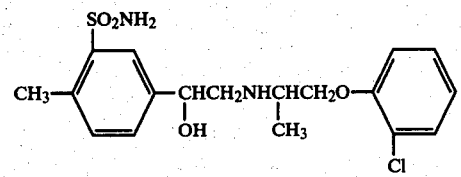

5-{1-Hydroxy-2-[2-(2-chlorophenoxy)-1-methyl-ethylamino]-ethyl}-2-methylbenzenesulfonamide
Physical and chemical properties
(1) Amorphous form
(2) Anal. (C$_{18}$H$_{23}$N$_2$O$_4$SCl)

|  | C(%) | H(%) | N(%) |
|---|---|---|---|
| Calcd.: | 54.20 | 5.81 | 7.02 |
| Found: | 54.02 | 5.67 | 6.66 |

(3) NMR (CDCl$_3$) ppm:
1.15 (3H, d, CHC$\underline{H}_3$),

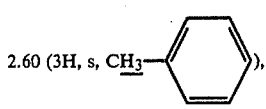
2.60 (3H, s, C$\underline{H}_3$—), 4.70 (1H, m, C$\underline{H}$OH).

EXAMPLE 7

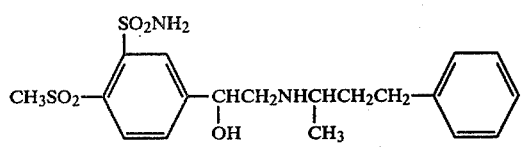

5-[1-Hydroxy-2-(1-methyl-3-phenylpropylamino)ethyl]-2-methylsulfonylbenzenesulfonamide Physical and chemical properties
(1) mp 136°–145° C.
(2) Anal. (C$_{19}$H$_{26}$N$_2$O$_5$S$_2$)

|  | C(%) | H(%) | N(%) |
|---|---|---|---|
| Calcd.: | 53.50 | 6.14 | 6.54 |
| Found: | 53.61 | 5.94 | 6.63 |

(3) NMR (d$_6$-DMSO) ppm:
1.00 (3H, d, CHC$\underline{H}_3$), 3.92 (3H, s, CH$_3$SO$_2$), 4.87 (3H, m, C$\underline{H}$OH).

EXAMPLE 8

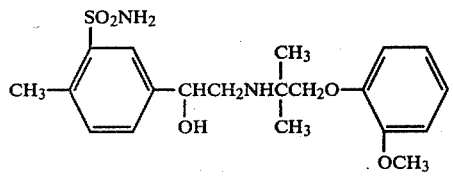

2-Bromo-5-[1-hydroxy-2-(1-methyl-3-phenylpropylamino)ethyl]benzenesulfonamide fumarate Physical and chemical properties
(1) Amorphous form
(2) Anal. (C$_{20}$H$_{25}$N$_2$O$_5$BrS)

|  | C(%) | H(%) | N(%) |
|---|---|---|---|
| Calcd.: | 49.49 | 5.19 | 5.77 |
| Found: | 49.76 | 5.28 | 5.51 |

(3) NMR (d$_6$-DMSO) ppm:
1.29 (3H, m, CHC$\underline{H}_3$), 5.02 (1H, m, C$\underline{H}$OH).

EXAMPLE 9

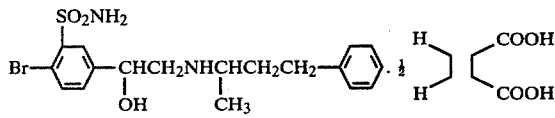

5-{1-Hydroxy-2-[2-(2-methoxyphenoxy-1,1-dimethylethylamino]ethyl}-2-methylbenzenesulfonamide Physical and chemical properties (1) mp 161°–162° C.
(2) Anal. (C$_{20}$H$_{28}$N$_2$O$_5$S)

|  | C(%) | H(%) | N(%) |
|---|---|---|---|
| Calcd.: | 58.80 | 6.91 | 6.86 |
| Found: | 58.52 | 7.11 | 6.67 |

(3) NMR (CDCl$_3$+d$_6$-DMSO) ppm:
1.17 (6H, s, C(CH$_3$)$_2$),

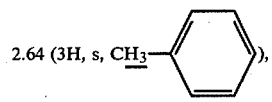
2.64 (3H, s, C$\underline{H}_3$—), 3.79 (3H, s, OCH$_3$), 4.64 (1H, q, C$\underline{H}$OH).

EXAMPLE 10

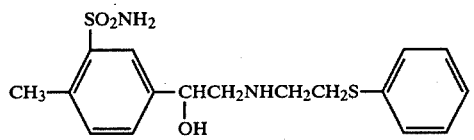

In 70 ml of ethanol was dissolved 2.26 g of 2-phenylthioethylamine. After adding to the solution 3 g of 5-epoxyethyl-2-methylbenzenesulfonamide, the mixture was refluxed for 6 hours. After cooling the reaction mixture, ethanol was distilled off under reduced pressure to provide a pale yellow oily product. The product was subjected to a silica gel column chromatography and eluted successively using a mixture of benzene and ethyl acetate of 1:1 by volume ratio, ethyl acetate, and a mixture of ethyl acetate and methanol of 9:1 by volume ratio to provide 850 mg of a pale yellow viscous oily product. The product was crystallized from a small amount of isopropanol and the crystals were recovered by filtration under suction and washed with ether to provide 385 mg of the colorless crystals of 5-[1-hydroxy-2-(2-phenylthioethylamino)ethyl]-2-methylbenzenesulfonamide. The product had the following physical and chemical properties.

(1) Melting point: 100.5°–103.5° C.
(2) Elemental analysis for C$_{17}$H$_{22}$N$_2$O$_3$S$_2$:

|  | C(%) | H(%) | N(%) | S(%) |
|---|---|---|---|---|
| Calculated: | 55.71 | 6.05 | 7.64 | 17.50 |
| Found: | 55.46 | 6.12 | 7.62 | 17.22 |

(3) Nuclear magnetic resonance spectra (CDCl$_3$+d$_6$-DMSO) ppm:

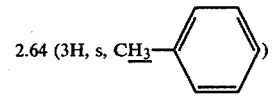
2.64 (3H, s, C$\underline{H}_3$—)

4.69 (1H, m, C$\underline{H}$OH)

By the similar procedure as in Example 10, the compounds of the following Examples 11–23 were produced.

EXAMPLE 11

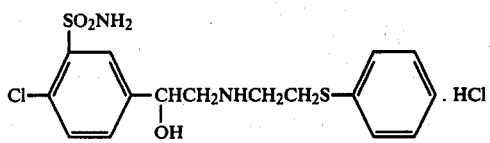

2-Chloro-5-[1-hydroxy-2-(2-phenylthioethylamino)ethyl]-benzenesulfonamide hydrochloride
Physical and chemical properties
(1) Amorphous form
(2) Anal. ($C_{16}H_{19}ClN_2O_3S_2 \cdot HCl$)

|  | C(%) | H(%) | N(%) |
|---|---|---|---|
| Calcd.: | 45.39 | 4.76 | 6.62 |
| Found: | 45.26 | 4.79 | 6.54 |

(3) NMR ($d_6$-DMSO+$CDCl_3$+$D_2O$+$Na_2CO_3$) ppm:
4.62 (1H, q, C$\underline{H}$OH)

EXAMPLE 12

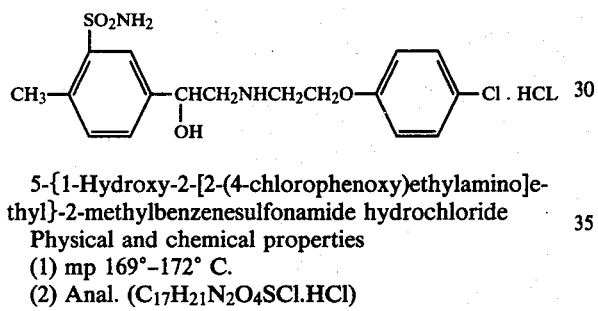

5-{1-Hydroxy-2-[2-(4-chlorophenoxy)ethylamino]ethyl}-2-methylbenzenesulfonamide hydrochloride
Physical and chemical properties
(1) mp 169°–172° C.
(2) Anal. ($C_{17}H_{21}N_2O_4SCl \cdot HCl$)

|  | C(%) | H(%) | N(%) |
|---|---|---|---|
| Calcd.: | 48.46 | 5.26 | 6.65 |
| Found: | 48.37 | 5.23 | 6.51 |

(3) NMR ($d_6$-DMSO+$D_2O$+$Na_2CO_3$) ppm:

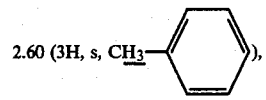
2.64 (3H, s, C$\underline{H_3}$—⬡), 4.80 (1H, m, C$\underline{H}$OH).

EXAMPLE 13

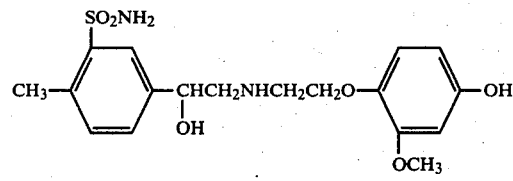

5-{1-Hydroxy-2-[2-(4-hydroxy-2-methoxyphenoxy)ethylamino]ethyl}-2-methylbenzenesulfonamide
Physical and chemical properties
(1) mp 189°–191° C.
(2) Anal. ($C_{18}H_{24}N_2O_6S$)

|  | C(%) | H(%) | N(%) |
|---|---|---|---|
| Calcd.: | 54.53 | 6.10 | 7.07 |
| Found: | 54.46 | 6.19 | 7.13 |

(3) NMR ($d_6$-DMSO) ppm:

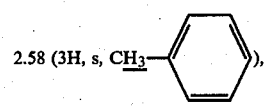
2.58 (3H, s, C$\underline{H_3}$—⬡), 3.68 (3H, s, $OCH_3$), 4.92 (1H, m, C$\underline{H}$OH).

EXAMPLE 14

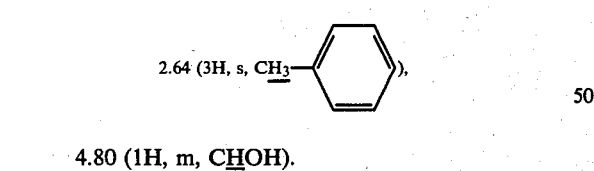

5-{2-[2-(4-allyl-2-methoxyphenoxy)ethylamino]-1-hydroxyethyl}-2-methylbenzenesulfonamide
Physical and chemical properties
(1) mp 152°–154° C.
(2) Anal. ($C_{21}H_{28}N_2O_5S$)

|  | C(%) | H(%) | N(%) |
|---|---|---|---|
| Calcd.: | 59.98 | 6.71 | 6.66 |
| Found: | 59.88 | 6.79 | 6.74 |

(3) NMR ($d_6$-DMSO) ppm:

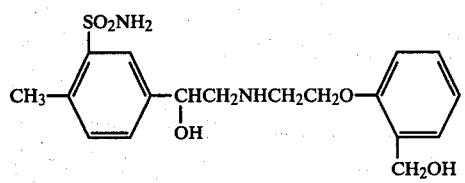
2.60 (3H, s, C$\underline{H_3}$—⬡), 3.76 (3H, s, $OCH_3$), 4.76 (1H, t, C$\underline{H}$OH).

EXAMPLE 15

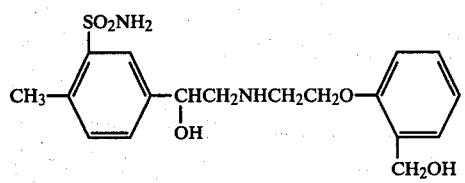

5-{1-Hydroxy-2-[2-(2-hydroxymethylphenoxy)ethylamino]-ethyl}-2-methylbenzenesulfonamide
Physical and chemical properties
(1) mp 129°–130° C.
(2) Anal. ($C_{18}H_{24}N_2O_5S$)

|  | C(%) | H(%) | N(%) |
|---|---|---|---|
| Calcd.: | 56.83 | 6.36 | 7.36 |
| Found: | 56.69 | 6.43 | 7.44 |

(3) NMR ($d_6$-DMSO) ppm:

2.56 (3H, s, C<u>H</u>₃—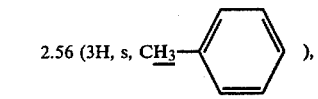), 4.03 (2H, t, CH₂C<u>H</u>₂O), 4.51 (2H, s, C<u>H</u>₂OH), 4.68 (1H, t, C<u>H</u>OH).

EXAMPLE 16

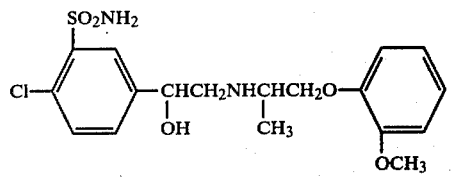

2-Chloro-5-{1-hydroxy-2-[2-(2-methoxyphenoxy)-1-methylethylamino]ethyl}benzenesulfonamide
Physical and chemical properties
(1) mp 176°–179° C.
(2) Anal. (C₁₈H₂₃ClN₂O₅S)

|  | C(%) | H(%) | N(%) |
|---|---|---|---|
| Calcd.: | 52.11 | 5.59 | 6.27 |
| Found: | 52.19 | 5.66 | 6.09 |

(3) NMR (d₆-DMSO+CDCl₃) ppm:
1.15 (3H, d, CHC<u>H</u>₃), 3.82 (3H, s, OCH₃), 4.75 (1H, m, C<u>H</u>OH).

EXAMPLE 17

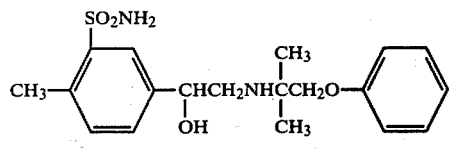

2-Methyl-5-[2-(1,1-dimethyl-2-phenoxyethylamino)-1-hydroxyethyl]benzenesulfonamide
Physical and chemical properties
(1) mp 184°–185° C.
(2) Anal. (C₁₉H₂₆N₂O₄S)

|  | C(%) | H(%) | N(%) |
|---|---|---|---|
| Calcd.: | 60.30 | 6.92 | 7.40 |
| Found: | 60.36 | 7.04 | 7.45 |

(3) NMR (d₆-DMSO) ppm:
1.12 (6H, s, C(CH₃)₂), 2.62 (3H, s, C<u>H</u>₃—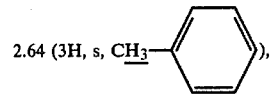), 3.76 (2H, s, CC<u>H</u>₂O), 4.68 (1H, t, C<u>H</u>OH).

EXAMPLE 18

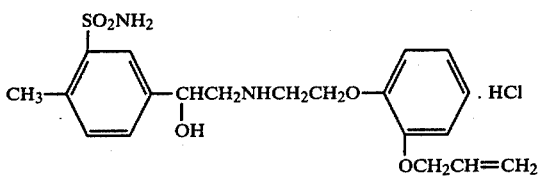

5-{2-[2-(2-Allyloxyphenoxy)ethylamino]-1-hydroxyethyl}-2-methylbenzenesulfonamide hydrochloride
Physical and chemical properties
(1) mp 141°–142° C.
(2) Anal. (C₂₀H₂₆N₂O₅S·HCl)

|  | C(%) | H(%) | N(%) |
|---|---|---|---|
| Calcd.: | 54.23 | 6.14 | 6.32 |
| Found: | 53.98 | 6.17 | 6.48 |

(3) NMR (d₆-DMSO+D₂O+Na₂CO₃) ppm:

2.64 (3H, s, C<u>H</u>₃—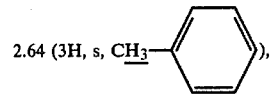), 4.78 (1H, m, C<u>H</u>OH), 6.08 (1H, m, OCH₂C<u>H</u>=CH₂).

EXAMPLE 19

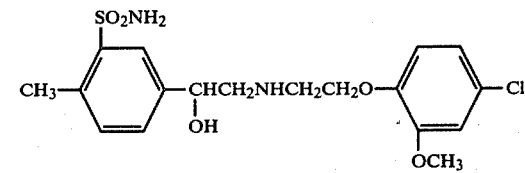

5-{1-Hydroxy-2-[2-(4-chloro-2-methoxyphenoxy)ethylamino]-ethyl}-2-methylbenzenesulfonamide
Physical and chemical properties
(1) mp 124°–126° C.
(2) Anal. (C₁₈H₂₃N₂O₅SCl)

|  | C(%) | H(%) | N(%) |
|---|---|---|---|
| Calcd.: | 52.11 | 5.59 | 6.75 |
| Found: | 52.24 | 5.48 | 6.69 |

(3) NMR (d₆-DMSO) ppm:

2.57 (3H, s, C<u>H</u>₃—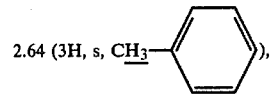), 3.77 (3H, s, OCH₃), 4.68 (1H, m, C<u>H</u>OH).

EXAMPLE 20

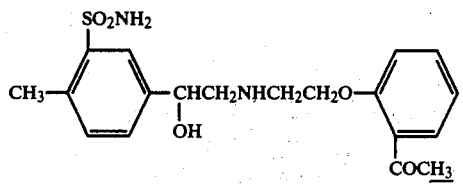

5-{2-[2-(2-Acetylphenoxy)ethylamino]-1-hydroxyethyl}-2-methylbenzenesulfonamide
Physical and chemical properties
(1) mp 104°–106° C.
(2) Anal. ($C_{19}H_{24}N_2O_5S$)

|  | C(%) | H(%) | N(%) |
|---|---|---|---|
| Calcd.: | 58.15 | 6.16 | 7.14 |
| Found: | 57.99 | 6.07 | 7.11 |

(3) NMR ($d_6$-DMSO) ppm:

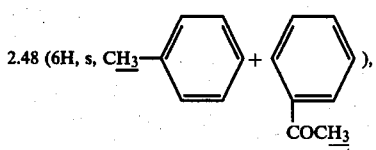

4.66 (1H, m, C$\underline{H}$OH).

EXAMPLE 21

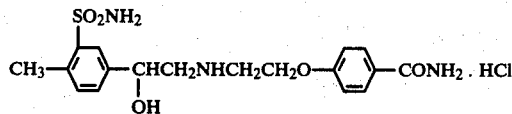

5-{2-[2-(4-Carbamoylphenoxy)ethylamino]-1-hydroxyethyl}-2-methylbenzenesulfonamide hydrochloride
Physical and chemical properties
(1) mp 180°–182° C.
(2) Anal. ($C_{18}H_{23}N_3O_5S\cdot HCl$)

|  | C(%) | H(%) | N(%) |
|---|---|---|---|
| Calcd.: | 50.29 | 5.63 | 9.77 |
| Found: | 50.11 | 5.78 | 9.51 |

(3) NMR ($d_6$-DMSO+$D_2O$+$Na_2CO_3$) ppm:

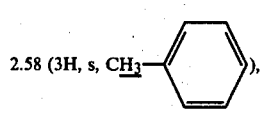

2.95 (2H, t, NC$\underline{H_2}$CH$_2$), 4.08 (2H, t, CH$_2$C$\underline{H_2}$O), 4.68 (1H, t, C$\underline{H}$OH).

EXAMPLE 22

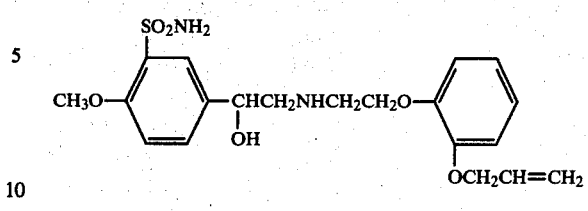

5-{1-Hydroxy-2-[2-(2-allyloxyphenoxy)ethylamino]ethyl}-2-methoxybenzenesulfonamide
Physical and chemical properties
(1) mp 156°–158° C.
(2) Anal. ($C_{20}H_{26}N_2O_6S$)

|  | C(%) | H(%) | N(%) |
|---|---|---|---|
| Calcd.: | 56.86 | 6.20 | 6.63 |
| Found: | 56.55 | 6.24 | 6.67 |

(3) NMR ($d_0$-DMSO) ppm:
2.72 (2H, d, CHC$\underline{H_2}$N), 2.92 (2H, t, NC$\underline{H_2}$CH$_2$), 3.90 (3H, s, OCH$_3$), 4.03 (2H, t, CH$_2$C$\underline{H_2}$O), 4.40–4.80 (3H, C$\underline{H_2}$CH=CH$_2$+C$\underline{H}$OH).

EXAMPLE 23

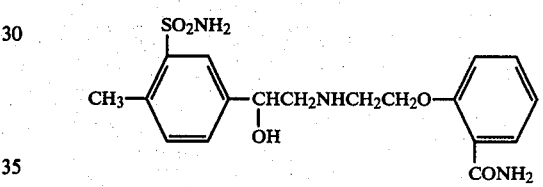

5-{1-Hydroxy-2-[2-(2-carbamoylphenoxy)ethylamino]ethyl}-2-methylbenzenesulfonamide
Physical and chemical properties
(1) mp 148°–150° C.
(2) Anal. ($C_{18}H_{23}N_3O_5S$)

|  | C(%) | H(%) | N(%) |
|---|---|---|---|
| Calcd.: | 54.95 | 5.89 | 10.68 |
| Found: | 55.10 | 5.91 | 10.74 |

(3) NMR ($d_6$-DMSO) ppm:

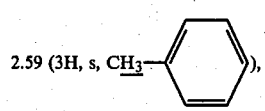

2.74 (2H, d, CHC$\underline{H_2}$N), 3.01 (2H, t, CH$_2$C$\underline{H_2}$N), 4.22 (2H, t, CH$_2$C$\underline{H_2}$O), 4.73 (1H, t, C$\underline{H}$OH).

EXAMPLE 24

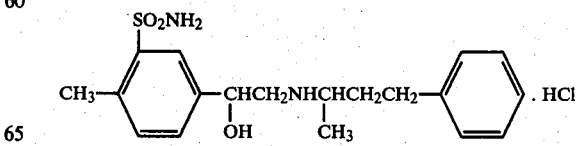

(1). A mixture of 12 g (0.05 mole) of N-benzyl-1-methyl-3-phenylpropylamine, 50 ml of methyl ethyl ketone, and 6.8 g (0.023 mole) of 5-bromoacetyl-2-methylbenzenesulfonamide was refluxed for 4 hours with stirring. After cooling the reaction mixture, ethyl ketone was distilled off under reduced pressure and the residue formed was dissolved in benzene. Then, ether was added to the solution and after removing the hydrobromide of N-benzyl-1-methyl-3-phenylpropylamine precipitated, the solvent was distilled off under reduced pressure to provide a viscous oily product.

(2). The product was dissolved in 50 ml of ethanol and after adding to the solution an excess amount of sodium boronhydride, the mixture was stirred for 2 hours at room temperature followed by distilling off ethanol under reduced pressure. The residue was dissolved in ethyl acetate and the ethyl acetate layer recovered was washed with water, dried over anhydrous sodium sulfate, and concentrated under reduced pressure to provide about 9 g of a pale yellow viscous oily product. The product was subjected to a silica gel column chromatography and eluted using benzene and then a mixture of benzene and ethyl acetate of 10:1 by volume ratio to provide 6.9 g of 5-[1-hydroxy-2-(N-benzyl-1-methyl-3-phenylpropylamino)ethyl]-2-methyl-benzene-sulfonamide as a colorless viscous oily product.

(3). In 50 ml of methanol was dissolved 2.8 g of the product obtained above. After adding thereto 1 g of 10% palladium charcoal, the product was subjected to a catalytic reduction at normal temperature and normal pressure. Then, after absorbing a theoretical amount of hydrogen, the catalyst was filtered away and the filtrate was distilled under reduced pressure to provide a colorless viscous oily product. The product was treated with ethanolic hydrochloric acid and 2.34 g. of a colorless amorphous solid product (hydrochloride) was obtained. The product was recrystallized from isopropanol to provide 1.8 g of the colorless crystals of 5-[1-hydroxy-2-(1-methyl-3-phenylpropylamino)ethyl]-2-methylbenzenesulfonamide hydrochloride. The product had the following physical and chemical properties.

(1) Melting point: 169°–172.5° C.
(2) Elemental analysis for $C_{19}H_{26}N_2O_3S \cdot HCl$:

|  | C(%) | H(%) | N(%) |
| --- | --- | --- | --- |
| Calculated: | 57.20 | 6.82 | 7.02 |
| Found: | 57.11 | 6.82 | 6.70 |

(3) Nuclear magnetic resonance spectra $(CDCl_3+D_2O+Na_2CO_3)$ ppm:
1.04 (3H, d, CHC$\underline{H}_3$)

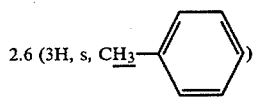

2.6 (3H, s, C$\underline{H}_3$—)

4.64 (1H, q, C$\underline{H}$OH)

EXAMPLE 25-67

By following the procedure as in Example 24, the compounds of this invention were also produced in Examples 25-67.

EXAMPLE 25

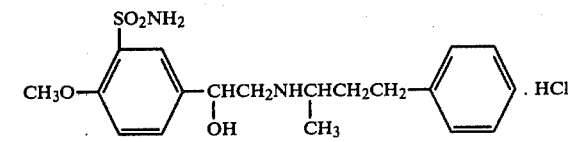

5-[1-Hydroxy-2-(1-methyl-3-phenylpropylamino)ethyl]-2-methoxybenzenesulfonamide hydrochloride
Physical and chemical properties
(1) mp 185°–188° C.
(2) Anal. $(C_{19}H_{26}N_2O_4S \cdot HCl)$

|  | C(%) | H(%) | N(%) |
| --- | --- | --- | --- |
| Calcd.: | 55.00 | 6.56 | 6.75 |
| Found: | 54.15 | 6.56 | 6.58 |

(3) NMR $(CDCl_3+D_2O+Na_2CO_3)$ ppm:
1.03 (3H, d, CHC$\underline{H}_3$), 3.90 (3H, s, OCH$_3$), 4.55 (1H, q, C$\underline{H}$OH).

EXAMPLE 26

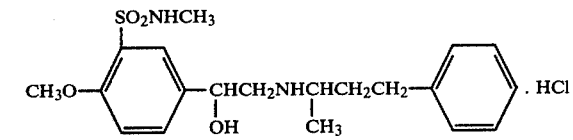

5-[1-Hydroxy-2-(1-methyl-3-phenylpropylamino)ethyl]-2-methoxy-N-methylbenzenesulfonamide hydrochloride
Physical and chemical properties
(1) mp 162°–164° C.
(2) Anal. $(C_{20}H_{28}N_2O_4S \cdot HCl)$

|  | C(%) | H(%) | N(%) |
| --- | --- | --- | --- |
| Calcd.: | 56.00 | 6.81 | 6.53 |
| Found: | 56.65 | 6.87 | 6.38 |

(3) NMR $(CDCl_3+D_2O+Na_2CO_3)$ ppm:
1.08 (3H, d, CHC$\underline{H}_3$), 2.54 (3H, s, NHC$\underline{H}_3$), 3.94 (3H, s, OCH$_3$), 4.62 (1H, q, C$\underline{H}$OH).

EXAMPLE 27

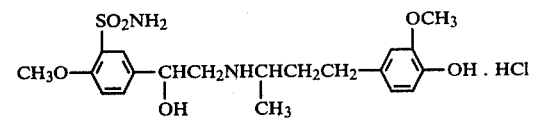

5-{1-Hydroxy-2-[3-(4-hydroxy-3-methoxyphenyl)-1-methylpropylamino]ethyl}-2-methoxybenzenesulfonamide hydrochloride
Physical and chemical properties
(1) Amorphous form
(2) Anal. $(C_{20}H_{28}N_2O_6S \cdot HCl)$

|  | C(%) | H(%) | N(%) |
| --- | --- | --- | --- |
| Calcd.: | 52.11 | 6.34 | 6.08 |
| Found: | 52.01 | 6.28 | 5.98 |

(3) NMR (D₂O) ppm:
1.41 (3H, d, CHC$\underline{H}_3$), 3.83 (3H, s, OCH₃), 3.97 (3H, s, OCH₃), 5.21 (1H, m, C$\underline{H}$OH)

EXAMPLE 28

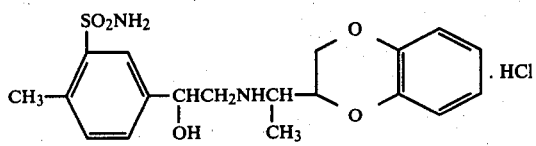

5-{1-Hydroxy-2-[1-1,4-benzodioxan-2-yl)ethylamino]ethyl}-2-methylbenzenesulfonamide hydrochloride (i₁') (This compound was produced using one (i₁') of the two isomers (i₁', i₂') of N-benzyl-1-methyl-3-phenylpropylamine.)
Physical and chemical properties
(1) Amorphous form
(2) Anal. (C₁₉H₂₄N₂O₅S.HCl)

|  | C(%) | H(%) | N(%) |
|---|---|---|---|
| Calcd.: | 53.20 | 5.88 | 6.53 |
| Found: | 53.31 | 5.76 | 6.44 |

(3) NMR (CDCl₃+D₂O+Na₂CO₃) ppm:
1.14 (3H, d, CHC$\underline{H}_3$),

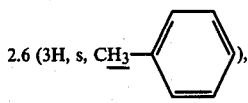

4.68 (1H, q, C$\underline{H}$OH).

EXAMPLE 29

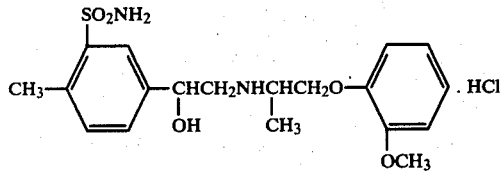

5-{1-Hydroxy-2-[2-(2-methoxyphenoxy)-1-methylethylamino]-ethyl}-2-methylbenzenesulfonamide hydrochloride
Physical and chemical properties
(1) Amorphous form
(2) Anal. (C₁₉H₂₆N₂O₅S.HCl)

|  | C(%) | H(%) | N(%) |
|---|---|---|---|
| Calcd.: | 52.95 | 6.32 | 6.50 |
| Found: | 52.51 | 6.49 | 6.45 |

(3) NMR (d₆-DMSO+CDCl₃+D₂O+Na₂CO₃) ppm:
1.2 (3H, d, CHC$\underline{H}_3$),

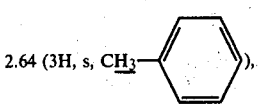

3.8 (3H, s, OCH₃), 4.75 (1H, m, C$\underline{H}$OH).

EXAMPLE 30

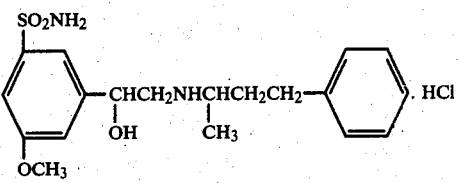

3-[1-Hydroxy-2-(1-methyl-3-phenylpropylamino)ethyl]-5-methoxybenzenesulfonamide hydrochloride
Physical and chemical properties
(1) Amorphous form
(2) Anal. (C₁₉H₂₆N₂O₄S.HCl)

|  | C(%) | H(%) | N(%) |
|---|---|---|---|
| Calcd.: | 55.00 | 6.56 | 6.75 |
| Found: | 54.97 | 6.60 | 6.59 |

(3) NMR (d₆-DMSO) ppm:
1.34 (3H, d, CHC$\underline{H}_3$), 3.85 (3H, s, OCH₃), 5.16 (1H, m, C$\underline{H}$OH).

EXAMPLE 31

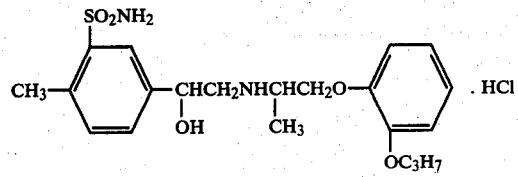

5-{1-Hydroxy-2-[2-(2-propoxyphenoxy)-1-methylethylamino]-ethyl}-2-methylbenzenesulfonamide hydrochloride
Physical and chemical properties
(1) Amorphous form
(2) Anal. (C₂₁H₃₀N₂O₅S.HCl)

|  | C(%) | H(%) | N(%) |
|---|---|---|---|
| Calcd.: | 54.95 | 6.81 | 6.10 |
| Found: | 54.76 | 6.91 | 6.05 |

(3) NMR (CDCl₃+D₂O+Na₂CO₃) ppm:
0.96 (3H, t, OCH₂CH₂C$\underline{H}_3$), 1.12 (3H, d, CHC$\underline{H}_3$),

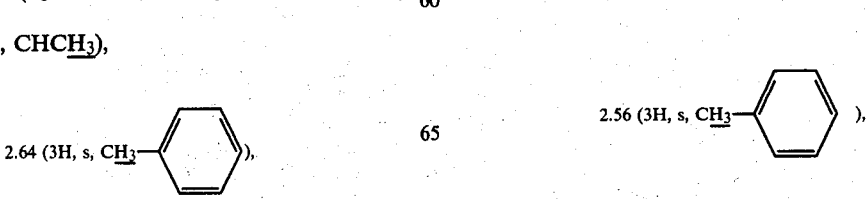

4.70 (1H, m, C$\underline{H}$OH).

EXAMPLE 32

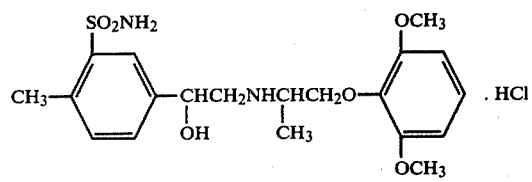

5-{1-Hydroxy-2-[2-(2,6-dimethoxyphenoxy)-1-methylethylamino]ethyl}-2-methylbenzenesulfonamide hydrochloride
Physical and chemical properties
(1) Amorphous form
(2) Anal. ($C_{20}H_{28}N_2O_6S \cdot HCl$)

|  | C(%) | H(%) | N(%) |
|---|---|---|---|
| Calcd.: | 52.11 | 6.34 | 6.08 |
| Found: | 51.89 | 6.54 | 5.92 |

(3) NMR ($d_6$-DMSO+CDCl$_3$+D$_2$O+Na$_2$CO$_3$) ppm:
1.12 (3H, d, CHC$\underline{H}_3$), 2.64 (3H, s, C$\underline{H}_3$-⌬), 3.80 (6H, s, OCH$_3$), 4.72 (1H, m, C$\underline{H}$OH).

EXAMPLE 33

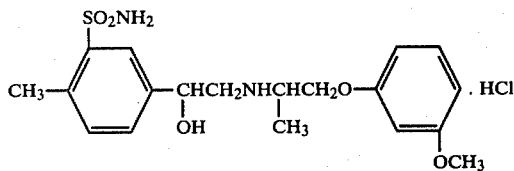

5-{1-Hydroxy-2-[2-(3-methoxyphenoxy)-1-methylethylamino]-ethyl}-2-methylbenzenesulfonamide hydrochloride
Physical and chemical properties
(1) Amorphous form
(2) Anal. ($C_{19}H_{26}N_2O_5S \cdot HCl$)

|  | C(%) | H(%) | N(%) |
|---|---|---|---|
| Calcd.: | 52.95 | 6.32 | 6.50 |
| Found: | 52.73 | 6.23 | 6.40 |

(3) NMR ($d_6$-DMSO) ppm:
1.36 (3H, d, CHC$\underline{H}_3$), 2.61 (3H, s, C$\underline{H}_3$-⌬), 3.76 (3H, s, OCH$_3$), 5.08 (1H, m, C$\underline{H}$OH).

EXAMPLE 34

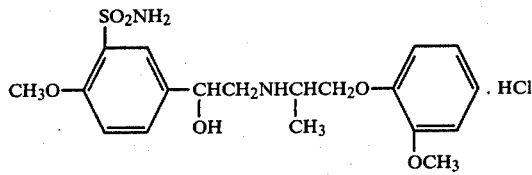

5-{1-Hydroxy-2-[2-(2-methoxyphenoxy)-1-methylethylamino]-ethyl}-2-methoxybenzenesulfonamide hydrochloride
Physical and chemical properties
(1) Amorphous form
(2) Anal. ($C_{19}H_{26}N_2O_6S \cdot HCl$)

|  | C(%) | H(%) | N(%) |
|---|---|---|---|
| Calcd.: | 51.06 | 6.09 | 6.27 |
| Found: | 50.81 | 6.02 | 6.25 |

(3) NMR (CDCl$_3$+D$_2$O+Na$_2$CO$_3$) ppm:
1.12 (3H, d, CHC$\underline{H}_3$), 3.75 (3H, s, OCH$_3$), 3.87 (3H, s, OCH$_3$), 4.62 (1H, m, C$\underline{H}$OH).

EXAMPLE 35

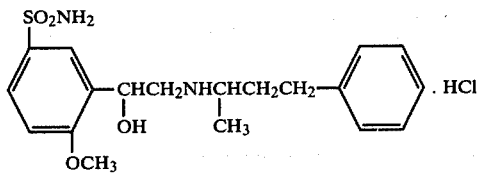

3-[1-Hydroxy-2-(1-methyl-3-phenylpropylamino)ethyl]-4-methoxybenzenesulfonamide hydrochloride
Physical and chemical properties
(1) Amorphous form
(2) Anal. ($C_{19}H_{26}N_2O_4S \cdot HCl$)

|  | C(%) | H(%) | N(%) |
|---|---|---|---|
| Calcd.: | 55.00 | 6.56 | 6.75 |
| Found: | 54.61 | 6.57 | 6.54 |

(3) NMR ($d_6$-DMSO) ppm:
1.33 (3H, d, CHC$\underline{H}_3$), 3.88 (3H, s, OCH$_3$), 5.25 (1H, m, C$\underline{H}$OH).

EXAMPLE 36

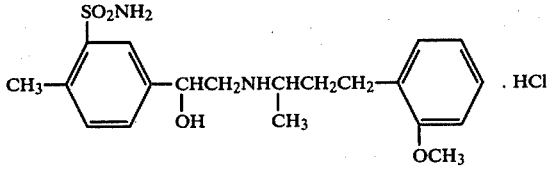

5-{1-Hydroxy-2-[3-(2-methoxyphenyl)-1-methylpropylamino]-ethyl}-2-methylbenzenesulfonamide hydrochloride
Physical and chemical properties
(1) mp 164°–165° C.
(2) Anal. ($C_{20}H_{28}N_2O_4S \cdot HCl$)

| | C(%) | H(%) | N(%) |
|---|---|---|---|
| Calcd.: | 56.00 | 6.81 | 6.53 |
| Found: | 55.83 | 6.90 | 6.66 |

(3) NMR (CDCl$_3$+d$_6$-DMSO+D$_2$O+Na$_2$CO$_3$) ppm:
1.10 (3H, d, CHC$\underline{H}_3$),

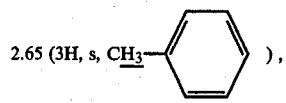

2.65 (3H, s, C$\underline{H}_3$—), 4.70 (1H, q, C$\underline{H}$OH).

EXAMPLE 37

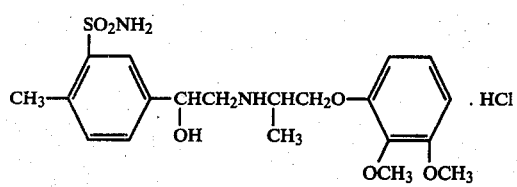

5-{1-Hydroxy-2-[2-(2,3-dimethoxyphenoxy)-1methylethylamino]ethyl}-2-methylbenzenesulfonamide hydrochloride
Physical and chemical properties
(1) Amorphous form
(2) Anal. (C$_{20}$H$_{28}$N$_2$O$_6$S.HCl.H$_2$O)

| | C(%) | H(%) | N(%) |
|---|---|---|---|
| Calcd.: | 50.15 | 6.52 | 5.85 |
| Found: | 49.74 | 6.18 | 5.26 |

(3) NMR (d$_6$-DMSO+CDCl$_3$+D$_2$O+Na$_2$CO$_3$) ppm:
1.18 (3H, d, CHC$\underline{H}_3$),

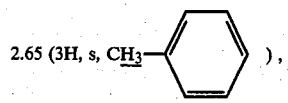

2.65 (3H, s, C$\underline{H}_3$—), 3.94 (3H, s, OCH$_3$), 4.78 (1H, t, C$\underline{H}$OH).

EXAMPLE 38

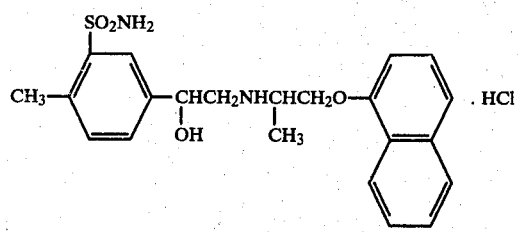

5-{1-Hydroxy-2-[1-methyl-2-(α-naphthoxy)ethylamino]ethyl}-2-methylbenzenesulfonamide hydrochloride
Physical and chemical properties
(1) Amorphous form
(2) Anal. (C$_{22}$H$_{26}$N$_2$O$_4$S.HCl)

| | C(%) | H(%) | N(%) |
|---|---|---|---|
| Calcd.: | 58.59 | 6.04 | 6.21 |
| Found: | 57.99 | 6.31 | 6.08 |

(3) NMR (d$_6$-DMSO+CDCl$_3$+D$_2$O+Na$_2$CO$_3$) ppm:
1.28 (3H, d, CHC$\underline{H}_3$),

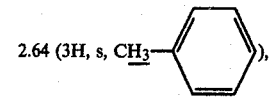

2.64 (3H, s, C$\underline{H}_3$—), 4.76 (1H, m, C$\underline{H}$OH).

EXAMPLE 39

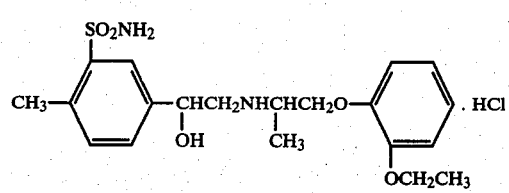

5-{1-Hydroxy-2-[2-(2-ethoxyphenoxy)-1-methylethylamino]-ethyl}-2-methylbenzenesulfonamide hydrochloride
Physical and chemical properties
(1) Amorphous form
(2) Anal. (C$_{20}$H$_{28}$N$_2$O$_5$S.HCl)

| | C(%) | H(%) | N(%) |
|---|---|---|---|
| Calcd.: | 53.99 | 6.57 | 6.30 |
| Found: | 53.67 | 6.77 | 6.39 |

(3) NMR (CDCl$_3$+D$_2$O+Na$_2$CO$_3$) ppm:
1.07–1.15 (3H, d, CHC$\underline{H}_3$), 1.34 (3H, t, C$\underline{H}_3$CH$_2$O),

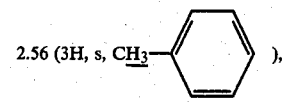

2.56 (3H, s, C$\underline{H}_3$—), 4.02 (2H, q, CH$_3$C$\underline{H}_2$O), 4.70 (1H, m, C$\underline{H}$OH).

EXAMPLE 40

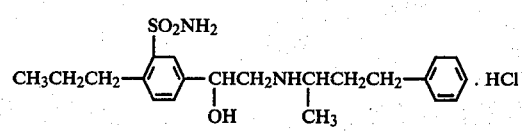

5-[1-Hydroxy-2-(1-methyl-3-phenylpropylamino)ethyl]-2-propylbenzenesulfonamide hydrochloride
Physical and chemical properties
(1) Amorphous form
(2) Anal. (C$_{21}$H$_{30}$N$_2$O$_3$S.HCl)

| | C(%) | H(%) | N(%) |
|---|---|---|---|
| Calcd.: | 59.07 | 7.32 | 6.56 |

-continued

| | C(%) | H(%) | N(%) |
|---|---|---|---|
| Found: | 58.79 | 7.21 | 6.35 |

(3) NMR (d₆-DMSO+D₂O+Na₂CO₃) ppm:
1.0 (3H, t, CH₂CH₂C$\underline{H}_3$), 1.08 (3H, d, CHC$\underline{H}_3$),
4.76 (1H, m, C$\underline{H}$OH).

EXAMPLE 41

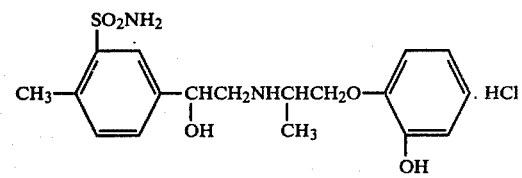

5-{1-Hydroxy-2-[2-(2-hydroxyphenoxy)-1-methylethylamino]-ethyl}-2-methylbenzenesulfonamide hydrochloride
Physical and chemical properties
(1) Amorphous form
(2) Anal. (C₁₈H₂₄N₂O₅S.HCl)

| | C(%) | H(%) | N(%) |
|---|---|---|---|
| Calcd.: | 51.86 | 6.04 | 6.72 |
| Found: | 51.92 | 6.14 | 6.66 |

(3) NMR (d₆-DMSO+D₂O+Na₂CO₃) ppm:
1.12 (3H, d, CHC$\underline{H}_3$), 2.65 (3H, s, C$\underline{H}_3$— 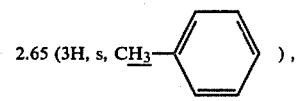 ), 4.84 (1H, m, C$\underline{H}$OH).

EXAMPLE 42

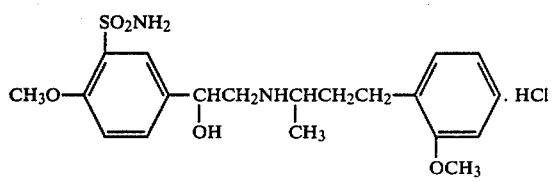

5-{1-Hydroxy-2-[3-(2-methoxyphenyl)-1-methylpropylamino]-ethyl}-2-methoxybenzenesulfonamide hydrochloride
Physical and chemical properties
(1) mp 180°–185° C.
(2) Anal. (C₂₀H₂₈N₂O₅S.HCl)

| | C(%) | H(%) | N(%) |
|---|---|---|---|
| Calcd.: | 53.98 | 6.57 | 6.30 |
| Found: | 54.02 | 6.62 | 6.27 |

(3) NMR (CDCl₃+D₂O+Na₂CO₃) ppm:
1.09 (3H, d, CHC$\underline{H}_3$), 4.57 (1H, m, C$\underline{H}$OH).

EXAMPLE 43

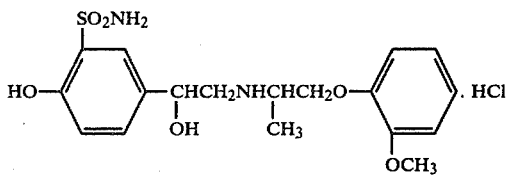

2-Hydroxy-5-{1-hydroxy-2-[2-(2-methoxyphenoxy)-1-methylethylamino]ethyl}benzenesulfonamide hydrochloride
Physical and chemical properties
(1) mp 194°–196° C.
(2) Anal. (C₁₈H₂₄N₂O₆S.HCl)

| | C(%) | H(%) | N(%) | S(%) |
|---|---|---|---|---|
| Calcd.: | 49.92 | 5.82 | 6.47 | 7.41 |
| Found: | 49.94 | 5.91 | 6.27 | 7.15 |

(3) NMR (d₆-DMSO) ppm:
1.38 (3H, d, CHC$\underline{H}_3$), 3.63 (3H, s, OCH₃), 5.00 (1H, m, C$\underline{H}$OH).

EXAMPLE 44

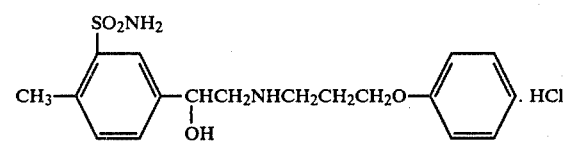

5-[1-Hydroxy-2-(3-phenoxypropylamino)ethyl]-2-methylbenzenesulfonamide hydrochloride
Physical and chemical properties
(1) mp 149°–151° C.
(2) Anal. (C₁₈H₂₄N₂O₄S.HCl)

| | C(%) | H(%) | N(%) |
|---|---|---|---|
| Calcd.: | 53.93 | 6.29 | 6.99 |
| Found: | 53.69 | 6.31 | 6.53 |

(3) NMR (CDCl₃+D₂O+Na₂CO₃) ppm:
1.84 (2H, m, CH₂C$\underline{H}_2$CH₂), 2.56 (3H, s, C$\underline{H}_3$— 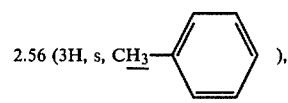 ), 3.90 (2H, t, CH₂C$\underline{H}_2$O), 4.71 (1H, m, C$\underline{H}$OH).

EXAMPLE 45

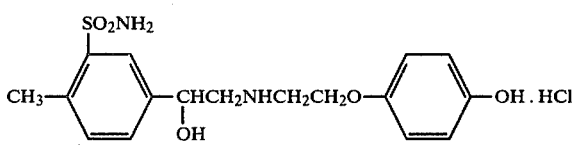

5-{1-Hydroxy-2-[2-(4-hydroxyphenoxy)ethylamino]ethyl}-2-methylbenzenesulfonamide hydrochloride
Physical and chemical properties (1) Amorphous form
(2) Anal. ($C_{17}H_{22}N_2O_5S \cdot HCl$)

|  | C(%) | H(%) | N(%) |
|---|---|---|---|
| Calcd.: | 50.68 | 5.75 | 6.95 |
| Found: | 50.32 | 5.89 | 6.78 |

(3) NMR ($d_6$-DMSO) ppm:

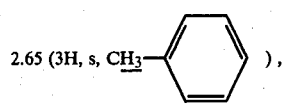

5.17 (1H, m, C$\underline{H}$OH).

EXAMPLE 46

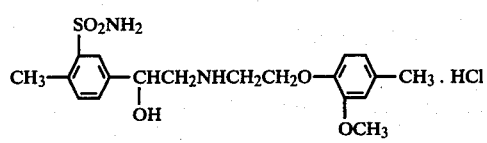

5-{1-Hydroxy-2-[2-(2-methoxy-4-methylphenoxy)ethylamino]-ethyl}-2-methylbenzenesulfonamide hydrochloride
Physical and chemical properties
(1) mp 198°–200° C.
(2) Anal. ($C_{19}H_{26}N_2O_5S \cdot HCl$)

|  | C(%) | H(%) | N(%) |
|---|---|---|---|
| Calcd.: | 52.96 | 6.31 | 6.50 |
| Found: | 52.61 | 6.36 | 6.56 |

(3) NMR ($d_6$-DMSO+CDCl$_3$+D$_2$O+Na$_2$CO$_3$) ppm:
2.26 and

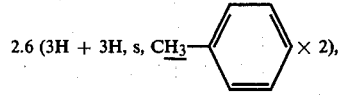

3.78 (3H, s, OCH$_3$), 4.76 (1H, t, C$\underline{H}$OH).

EXAMPLE 47

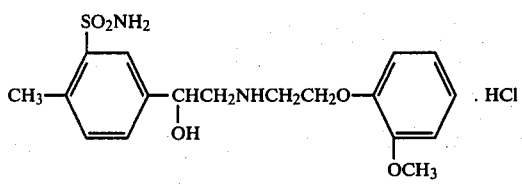

5-{1-Hydroxy-2-[2-(2-methoxyphenoxy)ethylamino]ethyl}-2-methylbenzenesulfonamide hydrochloride
Physical and chemical properties
(1) mp 166°–169° C.
(2) Anal. ($C_{18}H_{24}N_2O_5S \cdot HCl \cdot \frac{1}{2}H_2O$)

|  | C(%) | H(%) | N(%) |
|---|---|---|---|
| Calcd.: | 50.76 | 6.15 | 6.58 |

-continued

|  | C(%) | H(%) | N(%) |
|---|---|---|---|
| Found: | 51.02 | 6.22 | 6.33 |

(3) NMR (CDCl$_3$+D$_2$O+Na$_2$CO$_3$) ppm:

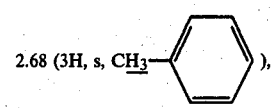

3.84 (3H, s, OCH$_3$), 4.12 (2H, t, NHCH$_2$C$\underline{H}_2$O),
4.83 (1H, m, C$\underline{H}$OH).

EXAMPLE 48

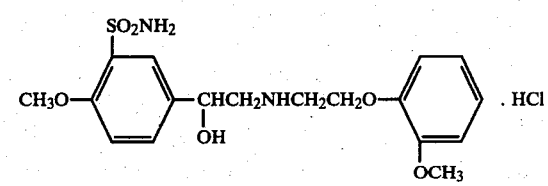

5-{1-Hydroxy-2-[2-(2-methoxyphenoxy)ethylamino]ethyl}-2-methoxybenzenesulfonamide hydrochloride
Physical and chemical properties
(1) mp 179°–180° C.
(2) Anal. ($C_{18}H_{24}N_2O_6S \cdot HCl$)

|  | C(%) | H(%) | N(%) |
|---|---|---|---|
| Calcd.: | 49.94 | 5.82 | 6.47 |
| Found: | 49.62 | 5.85 | 6.54 |

(3) NMR ($d_6$-DMSO) ppm:
3.72 and

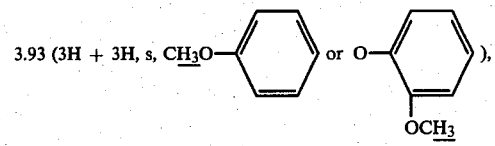

5.10 (1H, m, C$\underline{H}$OH).

EXAMPLE 49

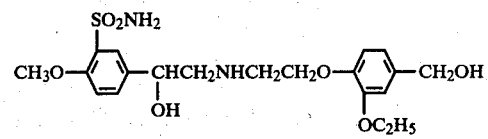

5-{1-Hydroxy-2-[2-(2-ethoxy-4-hydroxymethylphenoxy)ethylamino]ethyl}-2-methoxybenzenesulfonamide
Physical and chemical properties
(1) mp 175°–178° C.
(2) Anal. ($C_{20}H_{28}N_2O_7S$)

|  | C(%) | H(%) | N(%) |
|---|---|---|---|
| Calcd.: | 54.53 | 6.41 | 6.36 |

-continued

| | C(%) | H(%) | N(%) |
|---|---|---|---|
| Found: | 54.43 | 6.37 | 6.31 |

(3) NMR (d$_6$-DMSO) ppm:
1.21 (3H, t, C$\underline{H}_3$CH$_2$O), 3.94 (3H, s, OCH$_3$), 4.48 (2H, s, 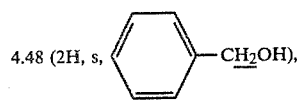), 5.06 (1H, m, C$\underline{H}$OH).

EXAMPLE 50

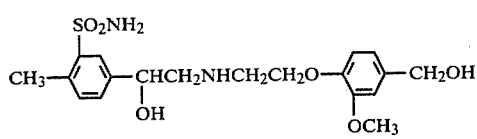

5-{1-Hydroxy-2-[2-(4-hydroxymethyl-1-methoxyphenoxy)-ethylamino]ethyl}-2-methylbenzenesulfonamide Physical and chemical properties
(1) mp 137°–139° C.
(2) Anal. (C$_{19}$H$_{26}$N$_2$O$_6$S)

| | C(%) | H(%) | N(%) |
|---|---|---|---|
| Calcd.: | 55.60 | 6.38 | 6.82 |
| Found: | 55.56 | 6.56 | 6.76 |

(3) NMR (d$_6$-DMSO) ppm:

2.56 (3H, s, C$\underline{H}_3$—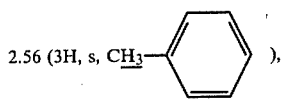), 2.75 (2H, d, CHC$\underline{H}_2$N), 2.92 (2H, t, NC$\underline{H}_2$CH$_2$),
3.73 (3H, s, OCH$_3$), 4.00 (2H, t, CH$_2$C$\underline{H}_2$O), 4.40 (2H, s, 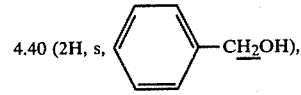—CH$_2$OH), 4.70 (1H, t, C$\underline{H}$OH).

EXAMPLE 51

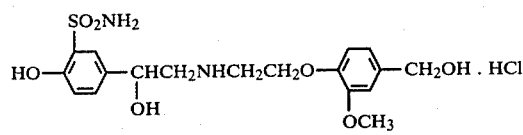

2-Hydroxy-5-{1-Hydroxy-2-[2-(4-hydroxymethyl-2-methoxyphenoxy)ethylamino]ethyl}benzenesulfonamide hydrochloride
Physical and chemical properties
(1) mp 161°–162.5° C.
(2) Anal. (C$_{18}$H$_{24}$N$_2$O$_7$S.HCl.H$_2$O)

| | C(%) | H(%) | N(%) |
|---|---|---|---|
| Calcd.: | 46.30 | 5.83 | 6.00 |
| Found: | 46.38 | 5.73 | 5.66 |

(3) NMR (d$_6$-DMSO+D$_2$O) ppm:
2.92 (2H, d, CHC$\underline{H}_2$N), 3.10 (2H, t, NC$\underline{H}_2$CH$_2$),
3.70 (3H, s, OCH$_3$), 4.10 (2H, t, CH$_2$C$\underline{H}_2$O), 4.42 (2H, s, 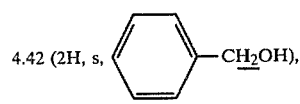—CH$_2$OH), 4.72 (1H, t, C$\underline{H}$OH).

EXAMPLE 52

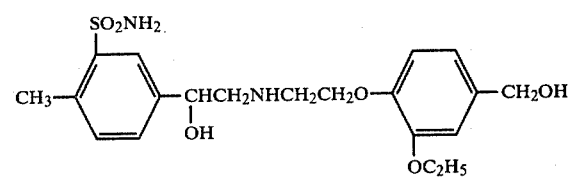

5-{1-Hydroxy-2-[2-(2-ethoxy-4-hydroxymethylphenoxy)ethylamino]ethyl}-2-methylbenzenesulfonamide Physical and chemical properties
(1) Amorphous form
(2) Anal. (C$_{20}$H$_{28}$N$_2$O$_6$S)

| | C(%) | H(%) | N(%) |
|---|---|---|---|
| Calcd.: | 56.59 | 6.65 | 6.60 |
| Found: | 56.48 | 6.71 | 6.49 |

(3) NMR (d$_6$-DMSO) ppm:
1.21 (3H, t, C$\underline{H}_3$CH$_2$O), 2.61 (3H, s, CH$_3$—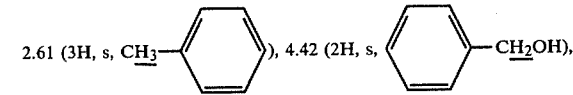), 4.42 (2H, s, 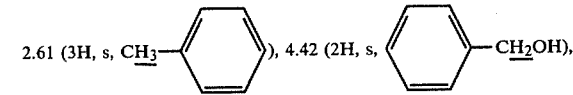—CH$_2$OH), 5.03 (1H, m, C$\underline{H}$OH).

EXAMPLE 53

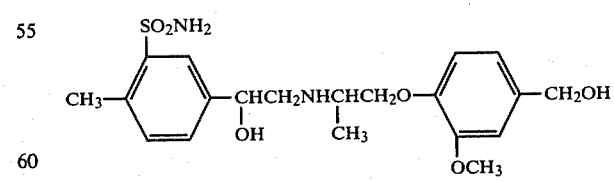

5-{1-Hydroxy-2-[2-(4-hydroxymethyl-2-methoxyphenoxy)-1-methylethylamino]ethyl}-2-methylbenzenesulfonamide
Physical and chemical properties
(1) Amorphous form
(2) Anal. (C$_{20}$H$_{28}$N$_2$S)

| | C(%) | H(%) | N(%) |
|---|---|---|---|
| Calcd.: | 56.59 | 6.65 | 6.60 |
| Found: | 56.79 | 6.50 | 6.46 |

(3) NMR (d₆-DMSO+D₂O) ppm:
1.00–1.16 (3H, d, CHC$\underline{H}_3$),

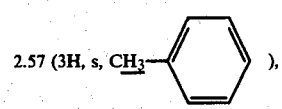

3.72 (3H, s, OCH₃),

4.72 (1H, m, C$\underline{H}$OH).

EXAMPLE 54

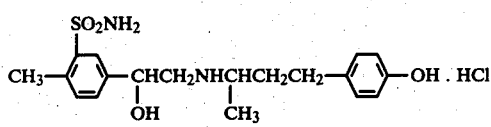

5-{1-Hydroxy-2-[3-(4-hydroxyphenyl)-1-methylpropylamino]-ethyl}-2-methylbenzenesulfonamide hydrochloride
Physical and chemical properties
(1) Amorphous form
(2) Anal. (C₁₉H₂₆N₂O₄S.HCl)

| | C(%) | H(%) | N(%) |
|---|---|---|---|
| Calcd.: | 55.00 | 6.56 | 6.75 |
| Found: | 55.19 | 6.47 | 6.55 |

(3) NMR (d₆-DMSO+D₂O+Na₂CO₃) ppm:
1.10 (3H, d, CHC$\underline{H}_3$),

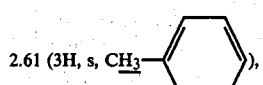

4.66 (1H, m, C$\underline{H}$OH).

EXAMPLE 55

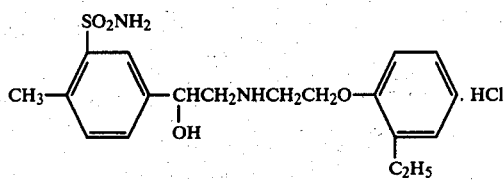

5-{1-Hydroxy-2-[2-(2-ethylphenoxy)ethylamino]ethyl}-2-methylbenzenesulfonamide hydrochloride
Physical and chemical properties
(1) mp 153°–155° C.

(2) Anal. (C₁₉H₂₆N₂O₄S.HCl)

| | C(%) | H(%) | N(%) |
|---|---|---|---|
| Calcd.: | 55.00 | 6.56 | 6.75 |
| Found: | 54.91 | 6.48 | 6.70 |

(3) NMR (d₆-DMSO+D₂O+Na₂CO₃) ppm:

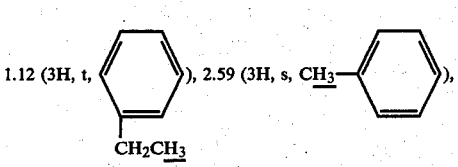

4.72 (1H, t, C$\underline{H}$OH).

EXAMPLE 56

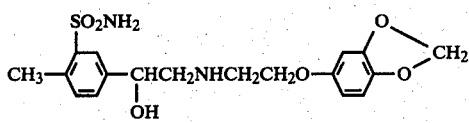

5-{1-Hydroxy-2-[2-(1,3-benzodioxol-5-yloxy)ethylamino]-ethyl}-2-methylbenzenesulfonamide
Physical and chemical properties
(1) mp 131°–133° C.
(2) Anal. (C₁₈H₂₂N₂O₆S)

| | C(%) | H(%) | N(%) |
|---|---|---|---|
| Calcd.: | 54.81 | 5.62 | 7.10 |
| Found: | 54.74 | 5.58 | 7.26 |

(3) NMR (d₆-DMSO) ppm:

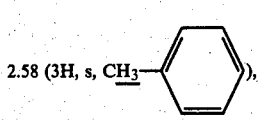

4.68 (1H, t, C$\underline{H}$OH),

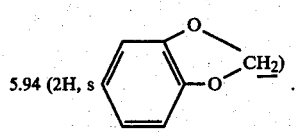

EXAMPLE 57

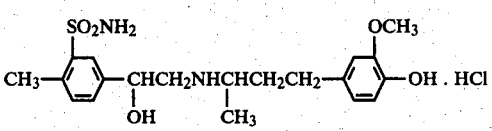

5-{1-Hydroxy-2-[3-(4-hydroxy-3-methoxyphenyl)-1-methylpropylamino]ethyl}-2-methylbenzenesulfonamide hydrochloride
Physical and chemical properties
(1) Amorphous form
(2) Anal. (C₂₀H₂₈N₂O₅S.HCl)

| | C(%) | H(%) | N(%) |
|---|---|---|---|
| Calcd.: | 53.98 | 6.57 | 6.30 |
| Found: | 53.57 | 6.72 | 6.15 |

(3) NMR (CDCl$_3$+D$_2$O+Na$_2$CO$_3$) ppm:
1.00 (3H, d, CHC$\underline{H}_3$),

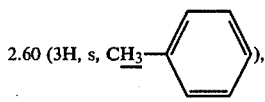
2.60 (3H, s, C$\underline{H}_3$—), 3.80 (3H, s, OCH$_3$), 4.58 (1H, m, C$\underline{H}$OH).

EXAMPLE 58

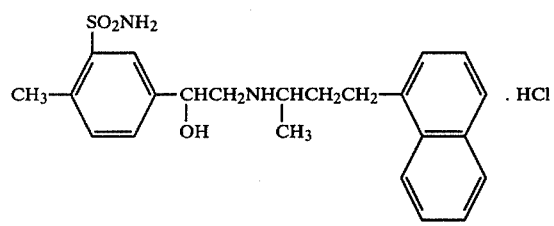

5-{1-Hydroxy-2-[1-methyl-3-(1-naphthyl)-propylamino]-ethyl}-2-methylbenzenesulfonamide hydrochloride
Physical and chemical properties
(1) Amorphous form
(2) Anal. (C$_{23}$H$_{28}$N$_2$O$_3$S.HCl)

| | C(%) | H(%) | N(%) |
|---|---|---|---|
| Calcd.: | 61.52 | 6.51 | 6.24 |
| Found: | 61.48 | 6.62 | 6.21 |

(3) NMR (d$_6$-DMSO+CDCl$_3$+D$_2$O+Na$_2$CO$_3$) ppm:
1.15 (3H, d, CHC$\underline{H}_3$),

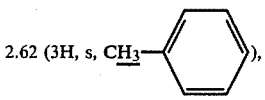
2.62 (3H, s, C$\underline{H}_3$—), 4.70 (1H, m, C$\underline{H}$OH).

EXAMPLE 59

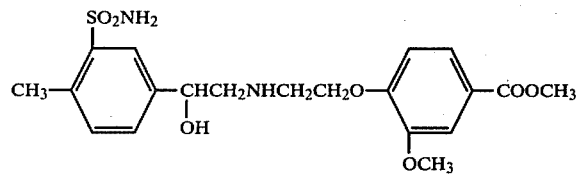

5-{2-[2-(2-methoxy-4-methoxycarbonylphenoxy)ethylamino]-1-hydroxyethyl}-2-methylbenzenesulfonamide
Physical and chemical properties
(1) mp 142°–144° C.
(2) Anal. (C$_{20}$H$_{26}$N$_2$O$_7$S)

| | C(%) | H(%) | N(%) |
|---|---|---|---|
| Calcd.: | 54.78 | 5.98 | 6.39 |
| Found: | 54.91 | 5.92 | 6.27 |

(3) NMR (CDCl$_3$) ppm:

2.64 (3H, s, C$\underline{H}_3$—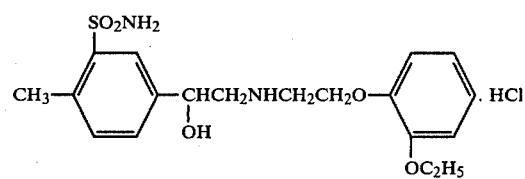), 3.08 (2H, t, NC$\underline{H}_2$CH$_2$), 3.88 (6H, s, COOCH$_3$+OCH$_3$), 4.17 (2H, t, CH$_2$C$\underline{H}_2$O), 4.76 (1H, t, C$\underline{H}$OH).

EXAMPLE 60

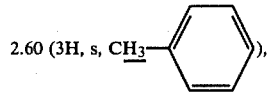

5-{1-Hydroxy-2-[2-(2-ethoxyphenoxy)ethylamino]ethyl}-2-methylbenzenesulfonamide hydrochloride
Physical and chemical properties
(1) mp 155°–157° C.
(2) Anal. (C$_{19}$H$_{26}$N$_2$O$_5$S.HCl)

| | C(%) | H(%) | N(%) |
|---|---|---|---|
| Calcd.: | 52.96 | 6.31 | 6.50 |
| Found: | 52.67 | 6.38 | 6.37 |

(3) NMR (d$_6$-DMSO) ppm:
1.15 (3H, t, C$\underline{H}_3$CH$_2$O), 2.60 (3H, s, C$\underline{H}_3$—), 3.96 (2H, q, CH$_3$C$\underline{H}_2$O), 5.12 (1H, t, C$\underline{H}$OH).

EXAMPLE 61

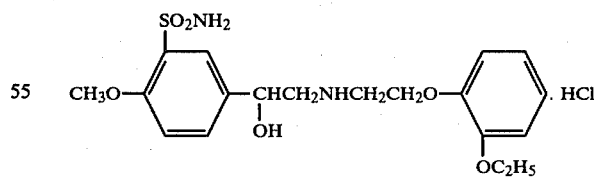

5-{1-Hydroxy-2-[2-(2-ethoxyphenoxy)ethylamino]ethyl}-2-methoxybenzenesulfonamide hydrochloride
Physical and chemical properties
(1) mp 183°–184.5° C.
(2) Anal. (C$_{19}$H$_{26}$N$_2$O$_6$S.HCl)

| | C(%) | H(%) | N(%) |
|---|---|---|---|
| Calcd.: | 51.06 | 6.09 | 6.27 |

|  | C(%) | H(%) | N(%) |
|---|---|---|---|
| Found: | 50.70 | 6.14 | 6.05 |

(3) NMR (d$_6$-DMSO) ppm:
1.16 (3H, t, C$\underline{H}_3$CH$_2$O), 3.80–4.10 (5H, OCH$_3$+CH$_3$C$\underline{H}_2$O), 5.12 (1H, t, C$\underline{H}$OH).

EXAMPLE 62

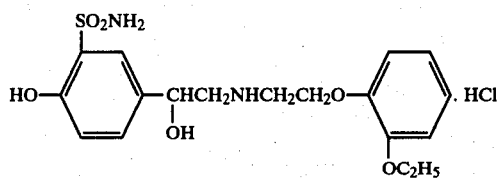

2-Hydroxy-5-{1-hydroxy-2-[2-(2-ethoxyphenoxy)ethylamino]-ethyl}benzenesulfonamide hydrochloride
Physical and chemical properties
(1) mp 199°–200.5° C.
(2) Anal. (C$_{18}$H$_{24}$N$_2$O$_6$S.HCl.H$_2$O)

|  | C(%) | H(%) | N(%) |
|---|---|---|---|
| Calcd.: | 47.94 | 6.04 | 6.21 |
| Found: | 47.94 | 5.75 | 6.21 |

(3) NMR (d$_6$-DMSO) ppm:
1.10 (3H, t, C$\underline{H}_3$CH$_2$O), 3.96 (2H, q, CH$_3$C$\underline{H}_2$O), 5.00 (1H, t, C$\underline{H}$OH).

EXAMPLE 63

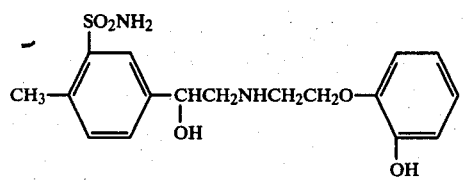

5-{1-Hydroxy-2-[2-(2-hydroxyphenoxy)ethylamino]ethyl}-2-methylbenzenesulfonamide
Physical and chemical properties
(1) mp 102°–104° C.
(2) Anal. (C$_{17}$H$_{22}$N$_2$O$_5$S)

|  | C(%) | H(%) | N(%) |
|---|---|---|---|
| Calcd.: | 55.72 | 6.05 | 7.64 |
| Found: | 55.61 | 6.21 | 7.59 |

(3) NMR (CDCl$_3$) ppm:

2.59 (3H, s, C$\underline{H}_3$—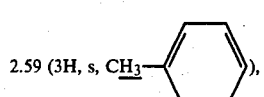), 2.90 (2H, t, CH$_2$C$\underline{H}_2$N), 4.02 (2H, t, CH$_2$C$\underline{H}_2$O), 4.79 (1H, t, C$\underline{H}$OH).

EXAMPLE 64

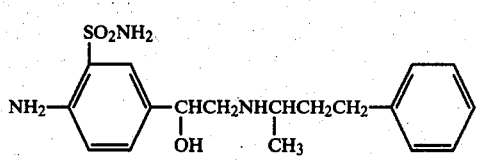

2-Amino-5-[1-hydroxy-2-(1-methyl-3-phenylpropylamino)ethyl]benzenesulfonamide
Physical and chemical properties
(1) Amorphous form
(2) Anal. (C$_{18}$H$_{25}$N$_3$O$_3$S)

|  | C(%) | H(%) | N(%) |
|---|---|---|---|
| Calcd.: | 59.48 | 6.93 | 11.56 |
| Found: | 59.69 | 7.02 | 11.48 |

(3) NMR (CDCl$_3$) ppm:
1.11 (3H, d, CHC$\underline{H}_3$), 4.59 (1H, t, C$\underline{H}$OH).

EXAMPLE 65

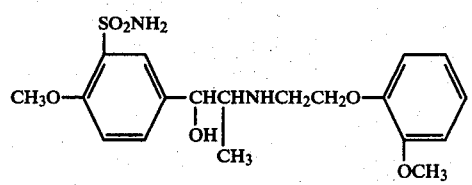

5-{1-Hydroxy-2-[2-(2-methoxyphenoxy)ethylamino]propyl}-2-methoxybenzenesulfonamide
Physical and chemical properties
(1) mp 151°–153° C.
(2) Anal. (C$_{19}$H$_{26}$N$_2$O$_6$S)

|  | C(%) | H(%) | N(%) |
|---|---|---|---|
| Calcd.: | 55.60 | 6.38 | 6.82 |
| Found: | 55.25 | 6.38 | 6.66 |

(3) NMR (d$_6$-DMSO) ppm:
0.79 (3H, d, CHC$\underline{H}_3$), 3.76 and 3.90 (3H + 3H, s, C$\underline{H}_3$O—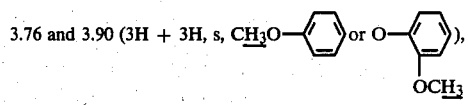), 4.30 (1H, d, C$\underline{H}$OH).

EXAMPLE 66

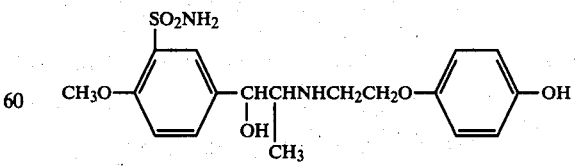

5-{1-Hydroxy-2-[2-(4-hydroxyphenoxy)ethylamino]propyl}-2-methoxybenzenesulfonamide
Physical and chemical properties
(1) mp 166°–168° C.
(2) Anal. (C$_{18}$H$_{24}$N$_2$O$_6$S)

|  | C(%) | H(%) | N(%) |
|---|---|---|---|
| Calcd.: | 54.53 | 6.10 | 7.07 |
| Found: | 54.31 | 6.16 | 6.94 |

(3) NMR (d$_6$-DMSO) ppm:
0.76 (3H, d, CHC$\underline{H}_3$), 4.26 (1H, d, C$\underline{H}$OH).

EXAMPLE 67

$$CH_3O-\underset{SO_2NH_2}{C_6H_3}-\underset{\underset{CH_3}{|}}{\underset{OH}{|}}CHCHNHCH_2CH_2CH_2-C_6H_5$$

5-[1-Hydroxy-2-(3-phenylpropylamino)propyl]-2-methoxybenzenesulfonamide

Physical and chemical properties
(1) mp 130°–132° C.
(2) Anal. (C$_{19}$H$_{26}$N$_2$O$_4$S)

|  | C(%) | H(%) | N(%) |
|---|---|---|---|
| Calcd.: | 60.30 | 6.92 | 7.40 |
| Found: | 60.16 | 6.96 | 7.15 |

(3) NMR (d$_6$-DMSO) ppm:
0.73 (3H, d, CHC$\underline{H}_3$), 3.88 (3H, s, OCH$_3$), 4.26 (1H, d, C$\underline{H}$OH).

EXAMPLE 68

$$CH_3O-\underset{SO_2NH_2}{C_6H_3}-\underset{\underset{}{}}{\underset{OH}{|}}CHCH_2NHCH_2CH_2O-\underset{OCH_3}{C_6H_4} \cdot HCl$$

In an autoclave were placed 10 g of 5-{N-benzyl-N-[2-(2-methoxyphenoxy)ethyl]aminoacetyl}-2-methoxybenzenesulfonamide, 100 ml of methanol, 1.85 ml of concentrated hydrochloric acid, and 1 g of 10% palladium charcoal. And the mixture was stirred for 6 hours at room temperature under hydrogen gas pressure. Then, the palladium charcoal was filtered away, a small amount of concentrated hydrochloric acid was added to the filtrate, the solvent was distilled off under reduced pressure, and then 50 ml. of ethanol was added to the residue thus obtained to form crystals, which were recovered by filtration under suction and dried to provide 8.28 g of the colorless crystals of 5-{1-hydroxy-2-[2-(2-methoxyphenoxy)ethylamino]ethyl}-2-methoxybenzenesulfonamide hydrochloride. The product was then recrystallized from ethanol. The product had the following physical and chemical properties.
(1) Melting point: 179°–181° C.
(2) Elemental analysis for C$_{18}$H$_{24}$N$_2$O$_6$S.HCl:

|  | C(%) | H(%) | N(%) |
|---|---|---|---|
| Calculated: | 49.94 | 5.82 | 6.47 |
| Found: | 49.85 | 5.79 | 6.43 |

(3) Nuclear magnetic resonance spectra (d$_6$-DMSO) ppm:

3.72 and 3.93 (3H + 3H, s, CH$_3$O—C$_6$H$_4$— or O—C$_6$H$_4$—OCH$_3$)

5.10 (1H, m, C$\underline{H}$OH)

EXAMPLE 69

$$CH_3-\underset{SO_2NH_2}{C_6H_3}-\underset{\underset{}{}}{\underset{OH}{|}}CHCH_2NHCH_2CH_2O-\underset{OCH_3}{C_6H_4} \cdot HCl$$

(1). In 200 ml of methanol was dissolved 20 g of 5-{1-hydroxy-2-[N-benzyl-2-(2-methoxyphenoxy)ethylamino]ethyl}-2-methylbenzenesulfonamide. After adding thereto 20 ml of ethanol containing about 10% hydrogen chloride and 1 g of 10% palladium charcoal, the mixture was shaken in hydrogen gas stream. When the absorption of hydrogen stopped, the catalyst was filtered away and the filtrate was distilled off under reduced pressure. The residue was dissolved in 100 ml of ethanol while it was hot and the solution was allowed to stand overnight in ice chamber, whereby 12.8 g of the α-type crystals of 5-{1-hydroxy-2-[2-(2-methoxyphenoxy)ethylamino]-ethyl}-2-methylbenzenesulfonamide were obtained as the colorless crystals. The physical and chemical properties of the product were as follows:
(1) Melting point: 169°–171° C.
(2) Elemental analysis for C$_{18}$H$_{24}$N$_2$O$_5$S.HCl:

|  | C(%) | H(%) | N(%) |
|---|---|---|---|
| Calculated: | 51.86 | 6.04 | 6.72 |
| Found: | 51.65 | 6.23 | 6.64 |

(3) Nuclear magnetic resonance spectra (d$_6$-DMSO+CDCl$_3$+D$_2$O+Na$_2$CO$_3$) ppm:

2.68 (3H, s, C$\underline{H}_3$—C$_6$H$_5$)

3.04 (2H, t, NC$\underline{H}_2$CH$_2$) 3.84 (3H, s, OCH$_3$)
4.12 (2H, t, C$\overline{H_2C}\underline{H}_2$O) 4.83 (1H, t, C$\underline{H}$OH)

(4) X-ray diffraction (electric power Cu-Kα 40KV, 30mA; λ = 1.5418A)

| distance (A) | Relative intensity (I)* |
|---|---|
| 15.50 | very strong |
| 7.76 | very strong |
| 6.07 | weak |
| 5.40 | weak |
| 5.16 | very strong |
| 4.67 | weak |
| 4.53 | strong |
| 3.87 | medium |
| 3.60 | medium |

| (4) X-ray diffraction (electric power Cu-Kα 40KV, 30mA; λ = 1.5418A) | |
|---|---|
| distance (A) | Relative intensity (I)* |
| 3.58 | medium |

*The relative intensity was shown by an optionally employed standard.

(2). In 250 ml of ethanol was dissolved a residue obtained by reducing 58 g of 5-{1-hydroxy-2-[N-benzyl-2-(2-methoxyphenoxy)ethylamino]ethyl}-2-methylbenzenesulfonamide as in above step (1) while it was hot. The solution was stirred vigorously under ice-cooling to precipitate colorless fine crystals, which were recovered by filtration under suction and washed with a small amount of ethanol to provide 46 g of the 62 -type crystals. The product had the following properties.

(1) Melting point: 158°-160° C.
(2) Elemental analysis for $C_{18}H_{24}N_2O_5S·HCl$:

|  | C(%) | H(%) | N(%) |
|---|---|---|---|
| Calculated: | 51.86 | 6.04 | 6.72 |
| Found: | 51.71 | 6.13 | 6.59 |

(3) Nuclear magnetic resonance spectra: same as those of the α-type.

| (4) X-ray diffraction (electric power Cu-Kα 40KV, 30mA; λ = 1.5418A) | |
|---|---|
| distance (A) | Relative intensity (I)* |
| 8.67 | medium |
| 6.76 | medium |
| 6.33 | weak |
| 5.90 | weak |
| 4.90 | medium |
| 4.74 | medium |
| 4.67 | strong |
| 4.46 | strong |
| 4.29 | strong |
| 3.92 | very strong |
| 3.72 | strong |
| 3.20 | strong |
| 3.12 | weak |

EXAMPLE 70

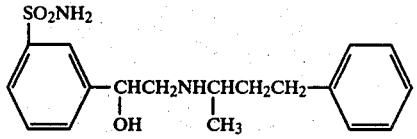

In 50 ml of methanol was dissolved 1.5 g of 2-chloro-5-[1-hydroxy-2-(1-methyl-3-phenylpropylamino)ethyl]-benzenesulfonamide. After adding thereto 0.5 g of 10% palladium charcoal, the catalytic reduction was performed at normal temperature and normal pressure. Then, after absorbing hydrogen until the absorption of hydrogen stopped, the catalyst was separated by filtration and washed with 200 ml of methanol. The methanol solution was combined with the filtrate and they were distilled under reduced pressure.

The residue was dissolved in 30 ml. of water and after removing undissolved matters, the solution was alkalified by the addition of an aqueous sodium hydroxide solution. The reaction mixture was then extracted with 100 ml of ethyl acetate under cooling. The extract was washed with water, dried over anhydrous magnesium sulfate, and then the solvent was distilled off under reduced pressure. The residue was subjected to a silica gel column chromatography, the product was eluted with a mixture of ethyl acetate and methanol of 9:1 by volume ratio, and the fractions containing the desired product were collected and dried under reduced pressure to provide 0.72 g of caramel-like solid 3-[1-hydroxy-2-(1-methyl-3-phenylpropylamino)-ethyl]benzenesulfonamide.

The compound obtained in this example coincided with the compound obtained in Example 1 in the nuclear magnetic resonance spectra, infrared absorption spectra, and thin layer chromatography.

By the similar procedure as in Example 70, the compound of the following Example 71 was produced.

EXAMPLE 71

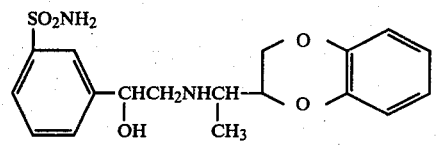

3-{1-Hydroxy-2-[1-(1,4-benzodioxan-2-yl)ethylamino]ethyl}-benzenesulfonamide
Physical and chemical properties
(1) Amorphous form
(2) Anal. ($C_{18}H_{22}N_2O_5S·HCl$)

|  | C(%) | H(%) | N(%) |
|---|---|---|---|
| Calcd.: | 51.97 | 5.57 | 6.74 |
| Found: | 51.76 | 5.63 | 6.61 |

(3) NMR (CDCl$_3$) ppm:
1.35 (3H, d, CHC$\underline{H}_3$), 5.13 (1H, m, C$\underline{H}$OH)

EXAMPLE 72

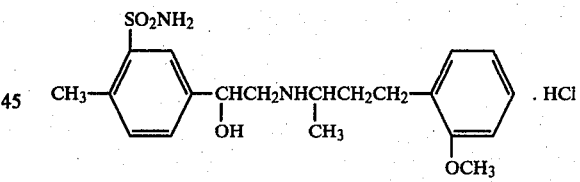

(1). In 1000 ml of methanol was dissolved 110 g of 5-{2-[N-benzyl-3-(2-methoxyphenyl)-1-methylpropylamino]acetyl}-2-methylbenzenesulfonamide. After adding thereto 10.2 g of sodium borohydride followed by stirring overnight at room temperature, methanol was distilled off under reduced pressure. The residue was dissolved in ethyl acetate and the solution was washed with water, dried over anhydrous magnesium sulfate, and distilled under reduced pressure to provide about 114 g of a diastereoisomer mixture i$_1$ and i$_2$ of 5-{1-hydroxy-2-[N-benzyl-3-(2-methoxyphenyl)-1-methylpropylamino]ethyl}-2-methylbenzenesulfonamide as a viscous oily product. The product was subjected to a silica gel column chromatography, the i$_1$ portion and the i$_2$ portion were recovered separately using a mixture of benzene and ethyl acetate of 5:1 by volume ratio, and each of them was repurified with a mixture of benzene and ethyl acetate of 9:1 by volume ratio, whereby the i$_1$ compound and the i$_2$ compound were obtained separately as colorless viscous oily materials.

(2). In 200 ml of methanol was dissolved 8.5 g of the i₁ compound obtained above. After adding thereto 1.0 g of 10% palladium charcoal and 0.1 ml of concentrated hydrochloric acid, the catalytic reduction was performed at normal temperature and normal pressure. After absorbing a theoretical amount of hydrogen, the catalyst was filtered away and the filtrate was distilled under reduced pressure. The residue was subjected to a silica gel column chromatography and the product was eluted using a mixture of chloroform and methanol of 9:1 by volume ratio to provide a colorless viscous oily product. The product was crystallized from isopropanol to provide 4.95 g of the white crystal of the i₁ compound of 5-{1-hydroxy-2-[3-(2-methoxyphenyl)-1-methylpropylamino]ethyl}-2-methylbenzenesulfonamide hydrochloride. The product had the following properties:

(1) Melting point: 176.5°–177.5° C.
(2) Elemental analysis for $C_{20}H_{29}N_2O_4SCl$:

|  | C(%) | H(%) | N(%) |
|---|---|---|---|
| Calculated: | 56.00 | 6.81 | 6.53 |
| Found: | 55.90 | 6.89 | 6.48 |

(3) Nuclear magnetic resonance spectra (CDCl₃+d₆-DMSO+D₂O+Na₂CO₃) ppm:
1.10 (3H, d, CHC$\underline{H}_3$)

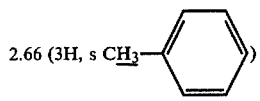

2.66 (3H, s C$\underline{H}_3$—⟨⟩)

3.82 (3H, s, OCH₃) 4.72 (1H, q, C$\underline{H}$OH)

(3). By following the same procedure as the above step (1) using 8.0 g of the i₂ compound, there was obtained 4.6 g of the white crystals of the i₂ compound of 5-{1-hydroxy-2-[3-(2-methoxyphenyl)-1-methylpropylamino]ethyl}-2-methylbenzenesulfonamide hydrochloride. The product had the following properties:

(1) Melting point: 151.5°–153.5° C.
(2) Elemental analysis for $C_{20}H_{29}N_2O_4SCl$:

|  | C(%) | H(%) | N(%) |
|---|---|---|---|
| Calculated: | 56.00 | 6.81 | 6.53 |
| Found: | 55.91 | 7.11 | 6.49 |

(3) Nuclear magnetic resonance spectra (CDCl₃+d₆-DMSO+D₂O+Na₂CO₃) ppm:
1.08 (3H, d, CHC$\underline{H}_3$)

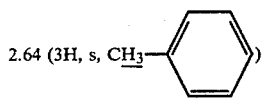

3.82 (3H, s, OCH₃) 4.68 (1H, q, CHOH)

EXAMPLE 73

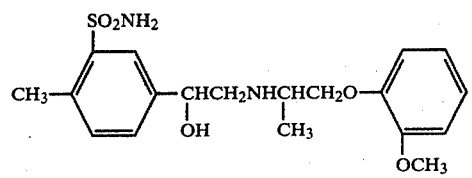

(1). In 1000 ml of methanol was dissolved 166.4 g of 5-{1-hydroxy-2-[N-benzyl-2-(2-methoxyphenoxy)-1-methylethylamino]ethyl}-2-methylbenzenesulfonamide. After adding thereto 13 g of 10% palladium charcoal, a theoretical amount of hydrogen was absorbed. Then, the catalyst was filtered away and methanol was distilled off under reduced pressure.

The residue was immersed in 200 ml of ethanol and the crystals were recovered by filtration to provide 26.6 g of the crude crystals of the isomer (i₂) of 5-{1-hydroxy-2-[2-(2-methoxyphenoxy)-1-methylethylamino]ethyl }-2-methylbenzenesulfonamide. The product was recrystallized four times from ethanol to provide the isomer (i₂) of 5-{1-hydroxy-2-[2-(2-methoxyphenoxy)-1-methylethylamino]ethyl}-2-methylbenzenesulfonamide The product had the following physical and chemical properties:

(1) Melting point: 153°–154° C.
(2) Elemental analysis for $C_{19}H_{26}N_2O_2S$:

|  | C(%) | H(%) | N(%) |
|---|---|---|---|
| Calculated: | 57.85 | 6.64 | 7.10 |
| Found: | 57.72 | 6.60 | 6.98 |

(3) Nuclear magnetic resonance spectra (d₆-DMSO) ppm:
1.10 (3H, d, CHC$\underline{H}_3$)

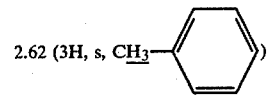

3.72 (3H, s, OCH₃) 4.74 (1H, m. C$\underline{H}$OH)

(2). On the other hand, the filtrate was allowed to stand overnight at room temperature and the crystals formed were recovered by filtration to provide 72.1 g of the crude crystals of the isomer (i₁) of 5-{1-hydroxy-2-[2-(2-methoxyphenoxy)-1-methylethylamino]ethyl}-2-methylbenzenesulfonamide. By repeating the recrystallization of the product four times from ethanol, the isomer (i₁) of 5-[1-hydroxy-2-[2-(2-methoxyphenoxy)-1-methylethylamino]ethyl}-2-methylbenzenesulfonamide was obtained. The product had the following physical and chemical properties.

(1) Melting point: 145°–147° C.
(2) Elemental analysis for $C_{19}H_{26}N_2O_5S$:

|  | C(%) | H(%) | N(%) |
|---|---|---|---|
| Calculated: | 57.85 | 6.64 | 7.10 |
| Found: | 57.75 | 6.66 | 7.06 |

(3) Nuclear magnetic resonance spectra (d₆-DMSO) ppm:
1.06 (3H, d, CHC$\underline{H}_3$)

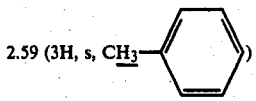

2.59 (3H, s, C$\underline{H}_3$)

3.76 (3H, s, OCH$_3$)  4.66 (1H, m, C$\underline{H}$CH)

EXAMPLE 74

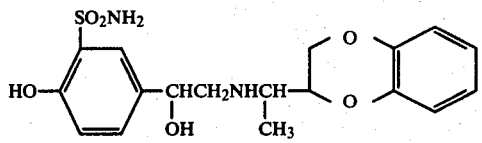

Production of (i$_1$-i$_1'$) and (i$_2$-i$_1'$) of 2-hydroxy-5-{1-hydroxy-2-[1-(1,4-benzodioxan-2-yl)ethylamino]ethyl}-benzenesulfonamide.

(1). A mixture of 10.76 g (0.04 mole) of N-benzyl-1-(1,4-benzodioxan-2-yl)ethylamine (i$_1'$), 7.68 g (0.02 mole) of 2-benzyloxy-5-bromoacetylbenzenesulfonamide, and 50 ml of methyl ethyl ketone was reluxed for 2 hours with stirring and then methyl ethyl ketone was distilled off under reduced pressure. The residue was subjected to a silica gel column chromatography and eluted using a mixture of chloroform and ethyl acetate of 2:1 by volume ratio to provide 9.6 g of the isomer (i$_1'$) of crude 2-benzyloxy-5-[N-benzyl-1-(1,4-benzodioxan-2-yl)ethylaminoacetyl]benzenesulfonamide.

(2). The product was dissolved in 300 ml of methanol and after adding thereto 3 g of sodium borohydride at room temperature, the mixture was stirred for 2 hours. Then, methanol was distilled off, 100 ml of water was added, and the product was extracted with 300 ml of ethyl acetate. The ethyl acetate layer was recovered, washed with water, dried over anhydrous magnesium sulfate, and ethyl acetate was distilled off under reduced pressure. The residue was subjected to a silica gel column chromatography and eluted using a mixture of chloroform and ethyl acetate of 2:1 by volume ratio to provide first 4.0 g. of (i$_1$-i$_1'$) of 2-benzyloxy-5-{1-hydroxy-2-[N-benzyl-1-(1,4-benzodioxan-2-yl)-ethylamino]ethyl}benzenesulfonamide and then 1.2 g of (i$_2$-i$_1'$) of 2-benzyloxy-5-{1-hydroxy-2-[N-benzyl-1-(1,4-benzodioxan-2-yl)ethylamino]ethyl}benzenesulfonamide.

Nuclear magnetic resonance spectra (CDCl$_3$) of [i$_1$-i$_1'$] obtained above ppm:
  1.19 (3H, d, CHC$\underline{H}_3$)
  4.60 (1H, q, C$\underline{H}$OH)

Nuclear magnetic resonance spectra (CDCl$_3$) of [i$_2$-i$_1'$] ppm:
  1.16 (3H, d, CHC$\underline{H}_3$)
  4.42 (3H, t, C$\underline{H}$OH)

(3)-(a). In 100 ml of methanol was dissolved 4.0 g of 2-benzyloxy-5-{1-hydroxy-2-[N-benzyl-1-(1,4-benzodioxan-2-yl)ethylamino]ethyl}benzenesulfonamide (i$_1$-i$_1'$) and after adding thereto 0.5 g of 10% palladium charcoal and one drop of alcoholic hydrochloric acid, a theoretical amount of hydrogen was absorbed therein at room temperature. Then, the catalyst was filtered away and after adding to the filtrate a slightly excess amount of alcoholic hydrochloric acid, methanol was distilled off under reduced pressure. Ether was added to the residue, whereby the residue was solidified. The solid obtained by filtration under suction was recrystallized from methanol to provide 2.5 g of the colorless crystals of 2-hydroxy-5-{1-hydroxy-2-[1-(1,4-benzodioxan-2-yl)ethylamino]ethyl}benzenesulfonamide hydrochloride (i$_1$-i$_1'$) having a melting point of 132°-134° C.

Elemental analysis for C$_{18}$H$_{22}$N$_2$O$_6$S.HCl:

|  | C(%) | H(%) | N(%) |
|---|---|---|---|
| Calculated: | 50.17 | 5.38 | 6.50 |
| Found: | 50.23 | 5.41 | 6.45 |

Nuclear magnetic resonance spectra (CDCl$_3$+d$_6$-DMSO):
  δ: 1.90 (3H, d, CHC$\underline{H}_3$) 5.20 (1H, m, C$\underline{H}$OH)

(3)-(b). In 50 ml of methanol was dissolved 1 g of 2-benzyloxy-5-{1-hydroxy-2-[N-benzyl-1-(1,4-benzodioxane-2-yl)ethylamino]ethyl}benzenesulfonamide (i$_2$-i$_1'$) and after adding thereto 0.5 g of 10% palladium charcoal and one drop of alcoholic hydrochloric acid, a theoretical amount of hydrogen was absorbed at room temperature. Then, the catalyst was filtered away and after adding to the filtrate a slightly excess amount of alcoholic hydrochloric acid, methanol was distilled off under reduced pressure. Ether was added to the residue, whereby the residue was solidified. The solid obtained by filtration under suction was recrystallized from isopropanol to provide 0.4 g of the colorless crystals of 2-hydroxy-5-{1-hydroxy-2-[1-(1,4-benzodioxan-2-yl)ethylamino]ethyl}benzenesulfonamide hydrochloride (i$_2$-i$_1'$) having a melting point of 205°-210° C.

Elemental analysis for C$_{18}$H$_{22}$N$_2$O$_6$S.HCl:

|  | C(%) | H(%) | N(%) |
|---|---|---|---|
| Calculated: | 50.17 | 5.38 | 6.50 |
| Found: | 49.96 | 5.35 | 6.56 |

Nuclear magnetic resonance spectra (CDCl$_3$+d$_6$-DMSO):
  δ: 1.91 (3H, d, CHC$\underline{H}_3$) 5.23 (1H, m, C$\underline{H}$OH)

By the similar procedure as in Example 74, the compound of the following Example 75 was produced.

EXAMPLE 75

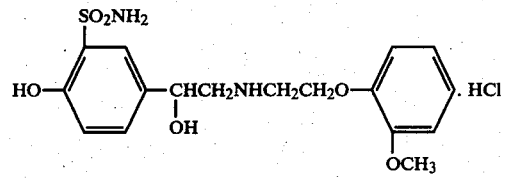

2-Hydroxy-5-{1-hydroxy-2-[2-(2-methoxyphenoxy)ethylamino]ethyl}benzenesulfonamide hydrochloride
Physical and chemical properties
(1) mp 192°-197° C.
(2) Anal. (C$_{17}$H$_{22}$N$_2$O$_6$S.HCl)

|  | C(%) | H(%) | N(%) |
|---|---|---|---|
| Calcd.: | 48.74 | 5.53 | 6.69 |
| Found: | 48.57 | 5.65 | 6.44 |

(3) NMR (CDCl$_3$+d$_6$-DMSO) ppm:
  3.76 (3H, s, OCH$_3$), 5.09 (1H, m, C$\underline{H}$OH).

EXAMPLE 76

(1). In 300 ml of methyl ethyl ketone were dissolved 7.3 g of 5-bromoacetyl-2-methoxybenzenesulfonamide and 12.4 g of N-benzyl-1-(1,4-benzodioxan-2-yl)ethylamine and after refluxing the solution for one hour, the solvent was distilled off. Ether was added to the residue and after filtering away the hydrobromide of secondary amine thus precipitated, the filtrate was evaporated to dryness. The sticky residue obtained was subjected to a silica gel column chromatography and eluted using a mixture of benzene and ethyl acetate of 95:5 by volume ratio. Then, the product was subjected to a silica gel thin layer chromatography using a mixture of benzene and ethyl acetate of 2:1 by volume ratio, 4.7 g of the isomer ($i_1'$) of 5-{N-benzyl-N-[1-(1,4-benzodioxan-2-yl)ethylamino]acetyl}-2-methoxybenzenesulfonamide showing $R_f$ of 5.7 and 4.2 g of the isomer ($i_2'$) of it shown Rf of 4.1 were obtained as oily materials.

(2). In 80 ml of methanol was dissolved 4 g of the aforesaid isomer ($i_1'$) of the aminoketone and after adding thereto 0.8 g of sodium borohydride with stirring under ice-cooling, the mixture was stirred further for 3 hours at room temperature. Then, the solvent was distilled off and the residue was extracted three times each time with 20 ml of chloroform. The extracts were combined with each other, washed with water, dried over anhydrous magnesium sulfate, and evaporated to dryness to provide 3.2 g of a sticky residue. The product was subjected to a silica gel column chromatography and eluted using a mixture of chloroform and methanol of 95:5 by volume ratio to provide 2.5 g of the powder of the isomer ($i_1'$) of 5-{1-hydroxy-2-[N-benzyl-N-[1-(1,4-benzodioxan-2-yl)ethylamino]]ethyl}-2-methoxybenzenesulfonamide.

By following the same procedure as in the case of producing the aforesaid isomer ($i_1'$) using 4 g of the isomer ($i_2'$) of the aminoketone, there was obtained 2.8 g of the caramel-like powder of the isomer ($i_2'$) of 5-{1-hydroxy-2-[N-benzyl-N-[1-(1,4-benzodioxan-2-yl)ethylamino]]ethyl}-2-methoxybenzenesulfonamide.

Nuclear magnetic resonance spectra (CDCl$_3$) of ($i_1'$) ppm:
  1.14 (3H, d, CHC$\underline{H}_3$)
  4.00 (3H, s, OCH$_3$)
  4.65 (1H, m, C$\underline{H}$OH)

Nuclear magnetic resonance spectra (CDCl$_3$) of ($i_2'$) ppm:
  1.07 (3H, d, CHC$\underline{H}_3$)
  3.94 (3H, s, OCH$_3$)
  4.57 (1H, m, C$\underline{H}$OH)

(3). A mixture of 2 g of the isomer ($i_1'$) of 5-{1-hydroxy-2-[N-benzyl-N-[1-(1,4-benzodioxan-2-yl)ethylamino]]ethyl}-2-methoxybenzenesulfonamide, 400 mg of 10% palladium charcoal 40 ml of methanol, and 0.4 mg of concentrated hydrochloric acid was subjected to catalytic reduction at normal temperature and normal pressure and after absorbing a theoretical amount of hydrogen, the catalyst was filtered away. Then, the filtrate was evaporated to dryness. The caramel-like residue thus formed was crystallized from isopropanol to provide 1.2 g of desired 5-{1-hydroxy-2-[1-(1,4-benzodioxan-2-yl)ethylamino]ethyl}-2-methoxybenzenesulfonamide hydrochloride ($i_1'$) having a melting point of 201°–202° C.

Elemental analysis for C$_{19}$H$_{24}$O$_6$N$_2$S.HCl:

|  | C(%) | H(%) | N(%) |
|---|---|---|---|
| Calculated: | 51.29 | 5.66 | 6.30 |
| Found: | 50.81 | 5.55 | 6.11 |

Nuclear magnetic resonance spectra (CDCl$_3$+D$_2$O+Na$_2$CO$_3$) ppm:
  1.16 (3H, d, CHC$\underline{H}_3$)
  3.94 (3H, s, OCH$_3$)
  4.66 (1H, m, C$\underline{H}$OH)

By following the same procedure as in the case of producing the aforesaid isomer ($i_1'$) using 2 g of the isomer ($i_2'$) of 5-{1-hydroxy-2-[N-benzyl-N-[1-(1,4-benzodioxan-2-yl)ethylamino]]ethyl}-2-methoxybenzenesulfonamide, 1.5 g of desired 5-{1-hydroxy-2-[1-(1,4-benzodioxan-2-yl)ethylamino]-ethyl}-2-methoxybenzenesulfonamide hydrochloride ($i_2'$) having a melting point of 215°–217° C. was obtained.

Elemental analysis for C$_{19}$H$_{24}$O$_6$N$_2$S.HCl:

|  | C(%) | H(%) | N(%) |
|---|---|---|---|
| Calculated: | 51.29 | 5.66 | 6.30 |
| Found: | 50.88 | 5.64 | 6.14 |

Nuclear magnetic resonance spectra (CDCl$_3$+D$_2$O+Na$_2$CO$_3$) ppm:
  1.14 (3H, d, CHC$\underline{H}_3$)
  3.96 (3H, s, OCH$_3$)
  4.59 (1H, m, C$\underline{H}$OH)

Then, the process of separating the racemic mixture ($i_1'$) based on the asymmetric carbon atoms *$_3$ and *$_4$ obtained in Example 76 and further the isomer ($i_1'$-$i_1$) and isomer ($i_1'$-$i_2$) based on the asymmmetric carbon atoms *$_1$ and *$_3$ is shown in (4) and the process of further reducing each isomer thus separated is shown in (5).

(4). 9 g Of the isomer ($i_1'$) of 5-{1-hydroxy-2-[N-benzyl-N-[1-(1,4-benzodioxan-2-yl)ethylamino]]ethyl}-2-methoxybenzenesulfonamide produced in above step (2) was subjected to a silica gel column chromatography and eluted using a mixture of benzene and ethyl acetate of 8:2 by volume ratio to provide 3.7 g of the isomer ($i_1'$-$i_1$) and 1.5 g of the isomer ($i_1'$-$i_2$) as well as 3.2 g of a mixture of isomers ($i_1'$-$i_1$) and ($i_1'$-$i_2$) each as powder.

Nuclear magnetic resonance spectra (CDCl$_3$) of ($i_1'$-$i_1$) ppm:
  1.20 (3H, d, CHC$\underline{H}_3$)
  3.94 (3H, s, OCH$_3$)
  4.60 (1H, m. C$\underline{H}$OH)

Nuclear magnetic resonance spectra (CDCl$_3$) of ($i_1'$-$i_2$) ppm:
  1.16 (3H, d, CHC$\underline{H}_3$)
  3.90 (3H, s, OCH$_3$)
  4.44 (1H, m, C$\underline{H}$OH)

(5). A mixture of 1.5 g of the isomer ($i_1'$-$i_1$) of 5-{1-hydroxy-2-[N-benzyl-N-[1-(1,4-benzodioxan-2-yl)ethylamino]ethyl}-2-methoxybenzenesulfonamide, 300 mg of 10% palladium charcoal, 30 ml of methanol, and 0.3 ml of concentrated hydrochloric acid was subjected to catalytic reduction at normal temperature and normal pressure and after absorbing a theoretical amount of hydrogen, the catalyst was filtered away. Then, the filtrate was evaporated to dryness. The syrupy residue was crystallized from isopropanol to provide 1.2 g of desired 5-{1-hydroxy-2-[1-(1,4-benzodioxan-2-yl)ethylamino]ethyl}-2-methoxybenzenesulfonamide hydrochloride (i₁'-i₁) having a melting point of 209°–211° C.

Elemental analysis for C₁₉H₂₄N₂O₆S.HCl:

|  | C(%) | H(%) | N(%) | Cl(%) |
|---|---|---|---|---|
| Calculated: | 51.29 | 5.66 | 6.30 | 7.97 |
| Found: | 51.00 | 5.74 | 6.47 | 7.92 |

Nuclear magnetic resonance spectra (d₆-DMSO) ppm:
 1.37 (3H, d, CHC$\underline{H}_3$)
 3.91 (3H, s, OCH₃)
 5.16 (1H, m, C$\underline{H}$OH)
Mass spectrum: 408 (M+).

By following the same procedure as in the case of producing the aforesaid isomer (i₁'-i₁) using 0.5 g of the isomer (i₁'-i₂) of 5-{1-hydroxy-2-[N-benzyl-N-[1-(1,4-benzodioxan-2-yl)ethylamino]]ethyl}-2-methoxybenzenesulfonamide, 0.35 g of desired 5-{1-hydroxy-2-[1-(1,4-benzodioxan-2-yl)-ethylamino]ethyl}-2-methoxybenzenesulfonamide hydrochloride (i₁'-i₂) having a melting point of 186°–188° C. was obtained.

Elemental analysis for C₁₉H₂₄N₂O₆S.HCl:

|  | C(%) | H(%) | N(%) | Cl(%) |
|---|---|---|---|---|
| Calculated: | 51.29 | 5.66 | 6.30 | 7.97 |
| Found: | 51.08 | 5.71 | 6.43 | 7.90 |

Nuclear magnetic resonance spectra (d₆-DMSO) ppm:
 1.34 (3H, d, CHC$\underline{H}_3$)
 3.90 (3H, s, OCH₃)
 5.14 (1H, m. C$\underline{H}$OH)
Mass spectrum: 408 (M+).

EXAMPLE 77

Medical composition:
Formulation for 1000 tablets:

| Active component | 100 g |
|---|---|
| Starch | 185 g |
| Lactose | 25 g |
| Magnesium stearate | 1.5 g |

The above components were granulated using a starch paste as a binder and then molded by a conventional manner.

What is claimed is:

1. Phenylethanolamine derivatives represented by the formula:

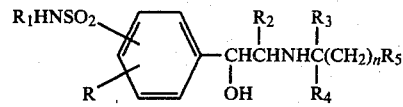

wherein R represents a member selected from the group consisting of a hydrogen atom, a halogen atom, a hydroxyl group, a lower alkyl group, a lower alkoxy group, a lower alkylthio group, and a lower alkylsulfonyl group,; R₁, R₂, R₃ and R₄, which may be the same or different, each represents a hydrogen atom or a lower alkyl group; R₅ represents an unsubstituted or substituted aryl group, benzodioxane ring group, aryloxy group, or arylthio group; said R₅ being, however, an unsubstituted or substituted benxodioxane ring group, aryloxy group, or arylthio group when R is a hydroxyl group; both of said R₃ and R₄ being, however, a hydrogen atom when R is a halogen atom; and n represents O or an integer of 1-3; and the acid addition salts thereof.

2. The compounds as claimed in claim 1 wherein said R₅ is a phenyl group or a phenoxy group each having a lower alkyl group, a hydroxyl group, a lower alkoxy group or a hydroxymethyl group as the substituent.

3. The compounds as claimed in claim 1 wherein said R₅ is a phenyl group or a phenoxy group each having a lower alkyl group, a hydroxyl group, a lower alkoxy group or a hydroxymethyl group as the substituent and said R is a lower alkyl group, a hydroxyl group, or a lower alkoxy group.

4. The compounds as claimed in claim 1 wherein said R₅ is a phenyl group or a phenoxy group each having a lower alkyl group, a hydroxyl group, a lower alkoxy group or a hydroxymethyl group as the substituent, said R is a lower alkyl group, a hydroxyl group, or a lower alkoxy group, and said R₁ is a hydrogen atom.

5. 5-{1-Hydroxy-2-[2-(2-methoxyphenoxy)-1-methylethylamino]ethyl}-2-methylbenzenesulfonamide or the acid addition salts thereof.

6. 5-{1-Hydroxy-2-[2-(2-methoxyphenoxy)ethylamino]ethyl}-2-methylbenzenesulfonamide or the acid addition salts thereof.

7. 5-{1-Hydroxy-2-[3-(2-methoxyphenyl)-1-methylpropylamino]ethyl}-2-methylbenzenesulfonamide or the acid addition salts thereof.

8. 5-{1-Hydroxy-2-[2-(2-methoxyphenoxy)ethylamino]ethyl}-2-methoxybenzenesulfonamide or the acid addition salts thereof.

9. The compounds as claimed in claim 1, wherein when R₅ is a substituted aryl group, benzodioxane ring group, aryloxy group, or arylthio group, said substituent is a hydroxyl group, a lower alkoxy group, a lower alkyl group, a halogen atom, a cyano group, a carbamoyl group, an aryl group, an aryloxy group, a methylenedioxy group, an ethylenedioxy group, or lower acyl group.

* * * * *